(12) United States Patent
Gilson et al.

(10) Patent No.: US 6,336,934 B1
(45) Date of Patent: Jan. 8, 2002

(54) EMBOLIC PROTECTION DEVICE

(75) Inventors: Paul Gilson, Moycullen; Eamon Brady, Elphin; Padraig Maher, Birr; David Vale, Dublin, all of (IE); Charles Taylor, Warninglid (GB)

(73) Assignee: Salviac Limited, Dublin (IR)

( * ) Notice: Subject to any disclaimer, the term of this patent is extended or adjusted under 35 U.S.C. 154(b) by 0 days.

(21) Appl. No.: 09/188,472

(22) Filed: Nov. 9, 1998

(30) Foreign Application Priority Data

Apr. 8, 1998 (IE) .............................................. 98 0267
Nov. 7, 1999 (IE) .............................................. 97 0789

(51) Int. Cl.⁷ ........................ A61M 29/20; A61B 17/22
(52) U.S. Cl. ...................................... 606/200; 606/159
(58) Field of Search ................................ 606/200, 194, 606/108; 604/96, 104–106

(56) References Cited

U.S. PATENT DOCUMENTS

| | | |
|---|---|---|
| 2,854,983 A | 10/1958 | Baskin |
| 3,334,629 A | 8/1967 | Cohn |
| 3,540,431 A | 11/1970 | Mebin-Uddin |
| 3,692,029 A | 9/1972 | Adair |
| 3,730,185 A | 5/1973 | Cook et al. |
| 3,952,747 A | 4/1976 | Kimmell |
| 4,295,464 A | 10/1981 | Shihata |
| 4,404,971 A | 9/1983 | LeVeen et al. |
| 4,423,725 A | 1/1984 | Baran et al. |
| 4,425,908 A | 1/1984 | Simon |
| 4,425,909 A | 1/1984 | Simon |
| 4,445,892 A | 5/1984 | Hussein et al. |
| 4,493,711 A | 1/1985 | Chin et al. |
| 4,512,762 A | 4/1985 | Spears |
| 4,585,000 A | 4/1986 | Hershenson |
| 4,610,662 A | 9/1986 | Weikl et al. |
| 4,619,246 A | 10/1986 | Molgaard-Nielsen et al. |

(List continued on next page.)

FOREIGN PATENT DOCUMENTS

| | | |
|---|---|---|
| EP | 0533511 A1 | 3/1993 |
| EP | 0 743 046 | 11/1996 |
| FR | 2 580 504 | 10/1986 |

(List continued on next page.)

*Primary Examiner*—Olik Chaudhuri
*Assistant Examiner*—(Vikki) Hoa B. Trinh
(74) *Attorney, Agent, or Firm*—Finnegan, Henderson, Farabow, Garrett & Dunner, LLp

(57) ABSTRACT

An embolic protection device has a collapsible filter element (105) mounted on a carrier such as a guidewire (101). The filter element (105) collapses into the outer end of a catheter (118) for deployment and retrieval through a vascular system of a patient. The filter element (105) has a collapsible filter body with a proximal inlet end and a distal outlet end. The proximal inlet end has inlet openings sized to allow blood and embolic material enter the filter body. The outlet end has outlet openings which allow through passage of blood but retain embolic material within the filter body. After use, the catheter (118) is movable along the guidewire (101) to engage the proximal end of the filter element and close the inlet openings before sliding over the filter element from the proximal end to the distal end to progressively collapse the filter body on the guidewire (101) for retrieval. The filter element (105) may conveniently be mounted on a tubular sleeve (104) which is slidable and rotatable on the guidewire (101) between spaced-apart stops (106, 120) on the guidewire (101) which allows some manipulation of the guidewire independently of the filter when the filter is in use.

38 Claims, 20 Drawing Sheets

U.S. PATENT DOCUMENTS

| | | |
|---|---|---|
| 4,619,294 A | 10/1986 | Molgaard-Nielse et al. |
| 4,650,466 A | 3/1987 | Luther |
| 4,723,549 A | 2/1988 | Wholey et al. |
| 4,790,812 A | 12/1988 | Hawkins, Jr. et al. |
| 4,794,928 A | 1/1989 | Kletschka |
| 4,873,978 A | 10/1989 | Ginsburg |
| 4,926,858 A | 5/1990 | Gifford, III et al. |
| 5,053,008 A | 10/1991 | Bajaj .......................... 604/104 |
| 5,108,419 A | 4/1992 | Reger et al. ................ 606/200 |
| 5,178,158 A | 1/1993 | de Toledo |
| 5,324,304 A | 6/1994 | Rasmussen ................. 606/200 |
| 5,329,942 A | 7/1994 | Gunther et al. ............. 128/898 |
| 5,405,329 A | 4/1995 | Durand |
| 5,662,671 A | 9/1997 | Barbut et al. |
| 5,669,933 A | 9/1997 | Simon et al. |
| 5,695,519 A | 12/1997 | Summers et al. ........... 606/200 |
| 5,766,203 A | 6/1998 | Imran et al. ................. 606/198 |
| 5,769,816 A | 6/1998 | Barbut et al. ................. 604/96 |
| 5,769,871 A | 6/1998 | Mers Kelly et al. ........ 606/200 |
| 5,795,322 A | 8/1998 | Boudewijn ................... 604/22 |
| 5,800,457 A | 9/1998 | Gelbfish ..................... 606/200 |
| 5,800,525 A | 9/1998 | Bachinski et al. |
| 5,814,064 A | 9/1998 | Daniel et al. ................ 606/200 |
| 5,827,324 A | 10/1998 | Cassell et al. |
| 5,848,964 A | 12/1998 | Samuels |
| 5,911,734 A | 6/1999 | Tsugita et al. |
| 5,941,869 A | 8/1999 | Patterson et al. |
| 5,954,745 A | 9/1999 | Gertler et al. |
| 5,976,172 A | 11/1999 | Homsma et al. |
| 5,993,469 A | 11/1999 | Mckenzie |
| 6,001,118 A | 12/1999 | Daniel et al. |
| 6,152,946 A | 11/2000 | Broome et al. |

FOREIGN PATENT DOCUMENTS

| | | |
|---|---|---|
| FR | 2 768 326 | 3/1999 |
| GB | 2020557 | 11/1979 |
| WO | WO8809683 | 12/1988 |
| WO | WO8907422 | 8/1989 |
| WO | WO 94/24946 | 11/1994 |
| WO | WO 95/34254 | 12/1995 |
| WO | WO 96/01591 | 1/1996 |
| WO | WO 97/42879 | 11/1997 |
| WO | WO 98/24377 | 6/1998 |
| WO | WO 98/33443 | 8/1998 |
| WO | WO 98/46297 | 10/1998 |
| WO | WO 98/49952 | 11/1998 |
| WO | WO 99/16382 | 4/1999 |
| WO | WO9923976 | 5/1999 |
| WO | WO 00/16705 | 3/2000 |

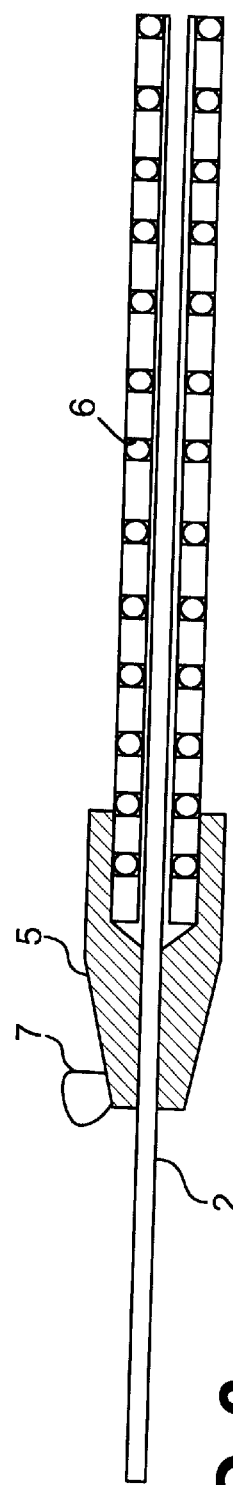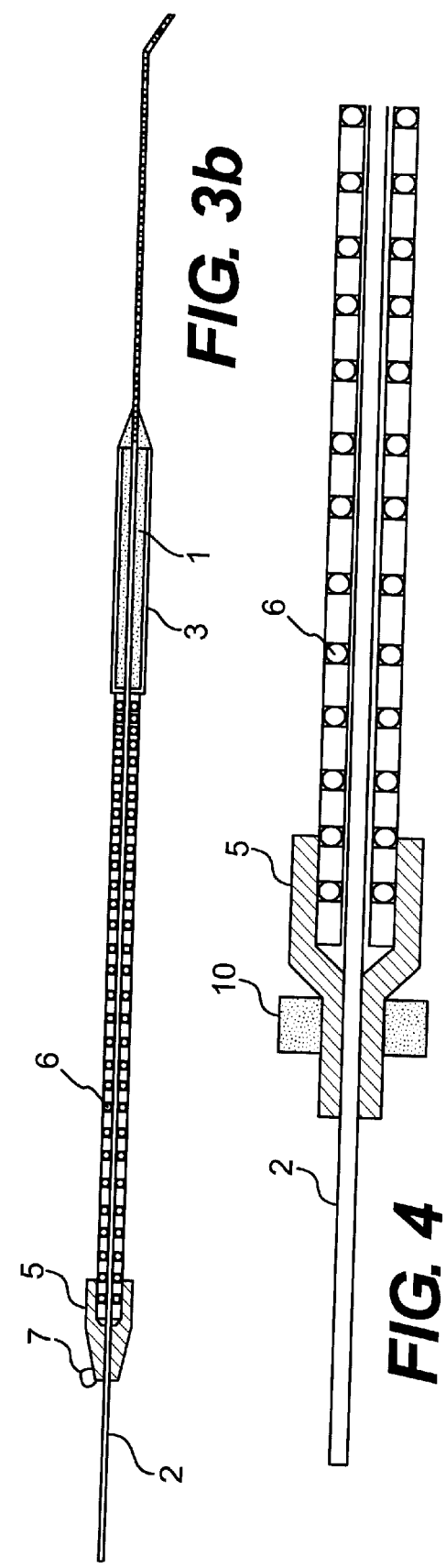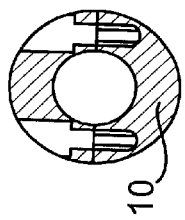

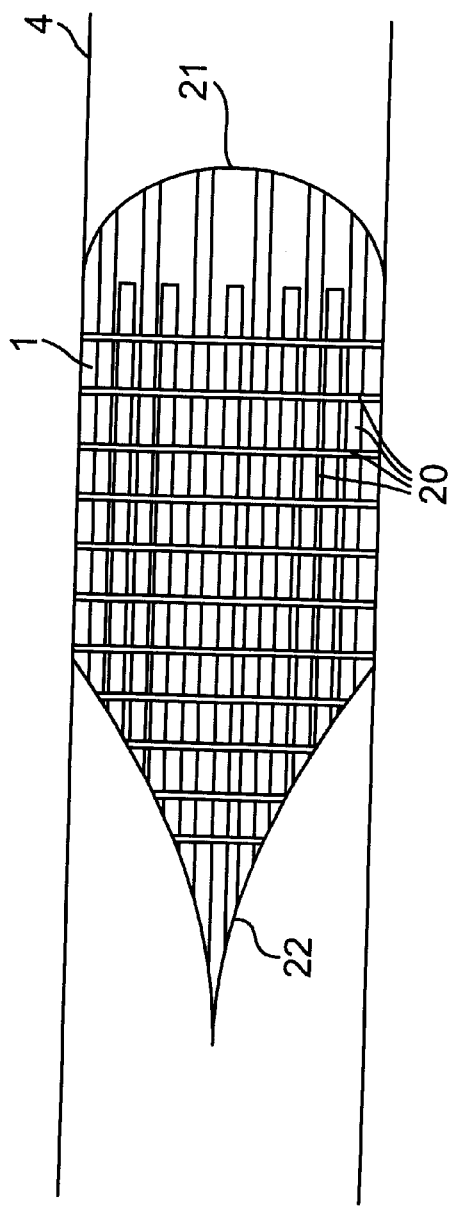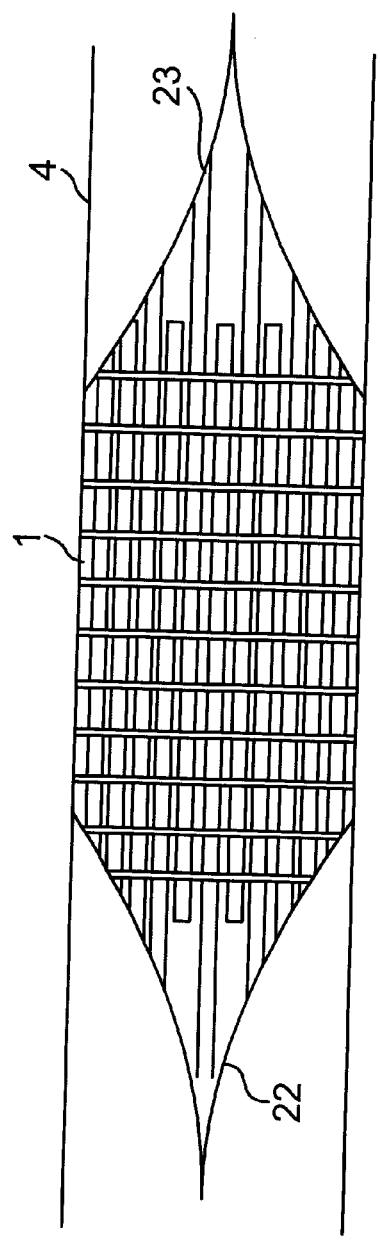

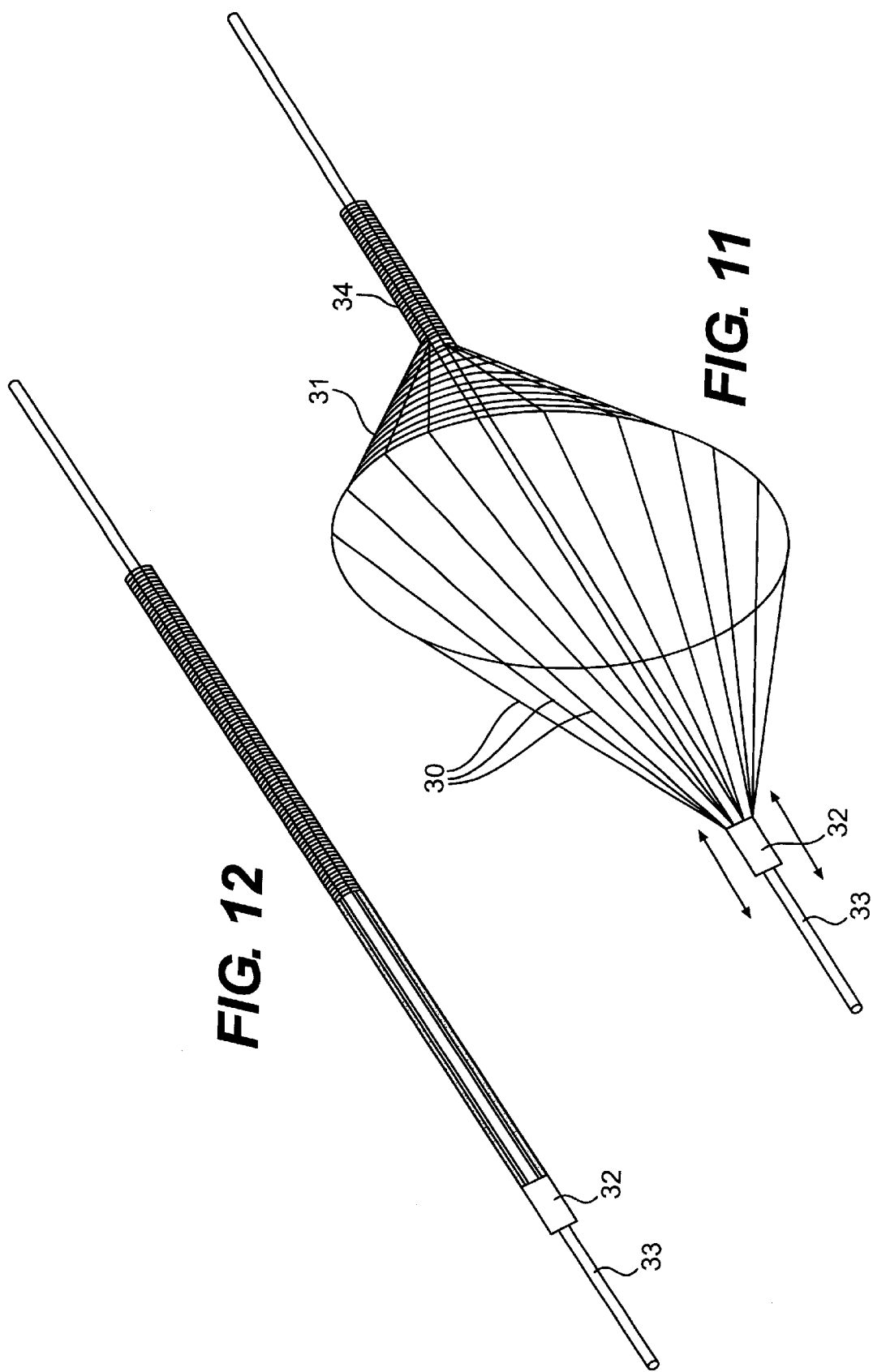

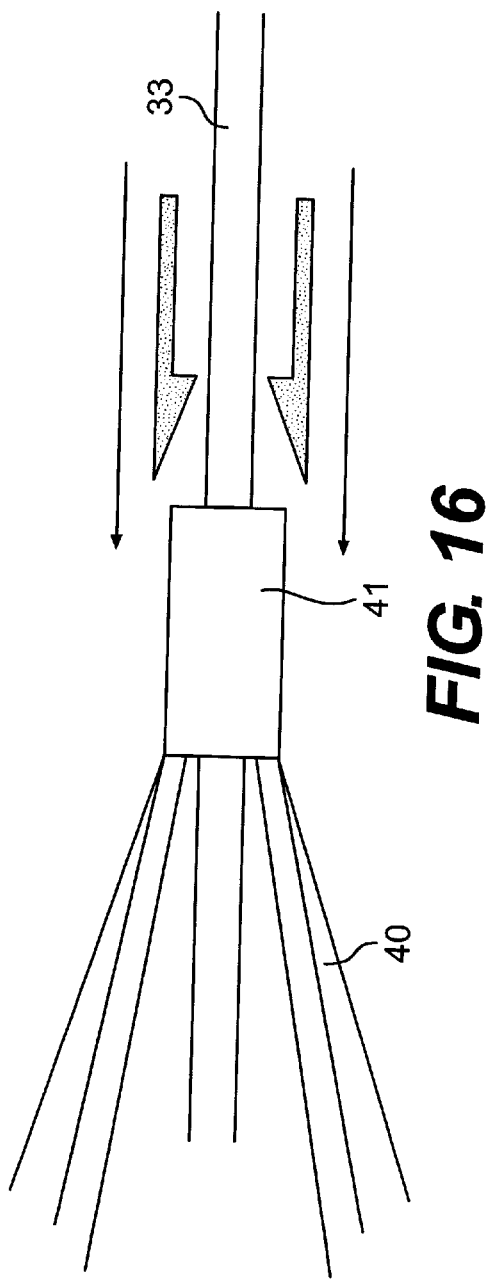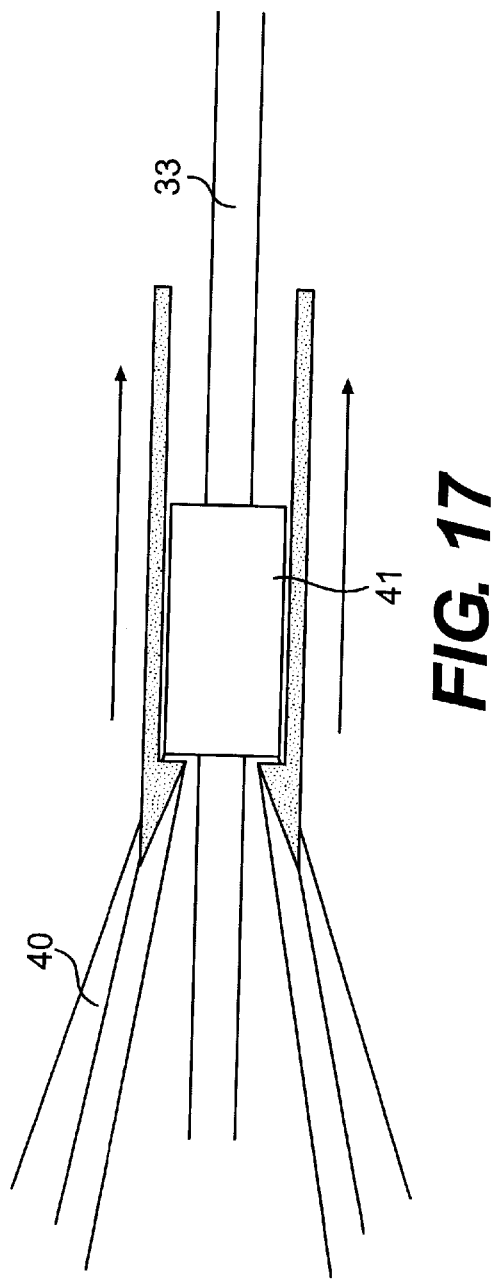

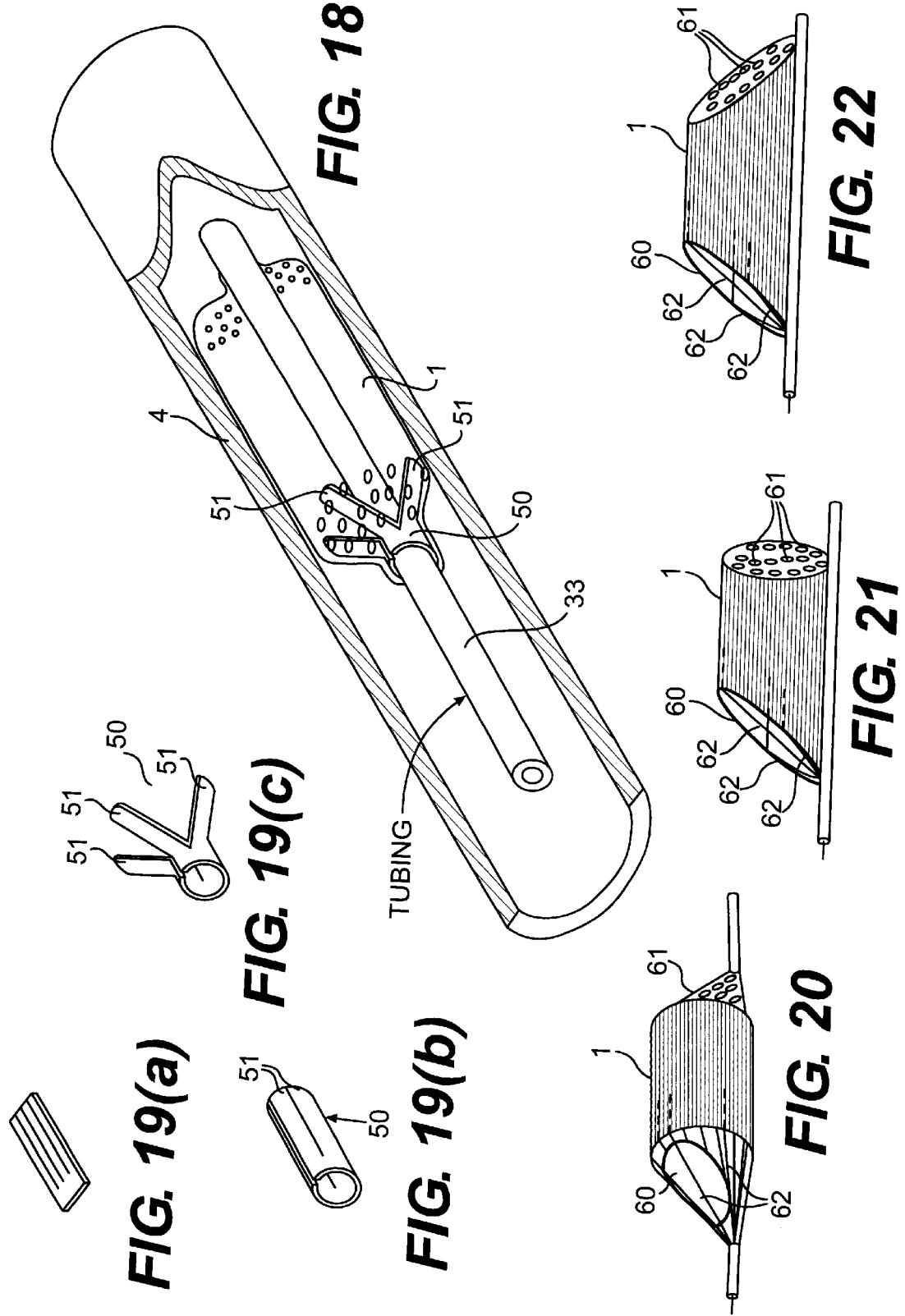

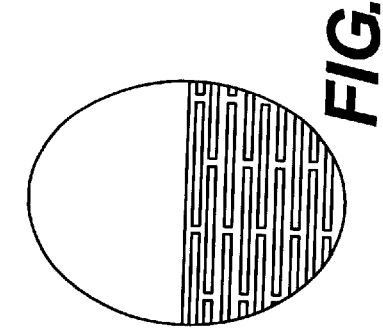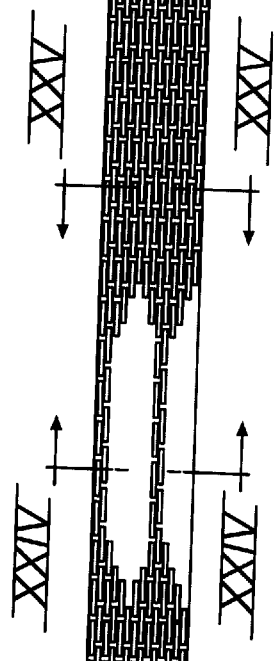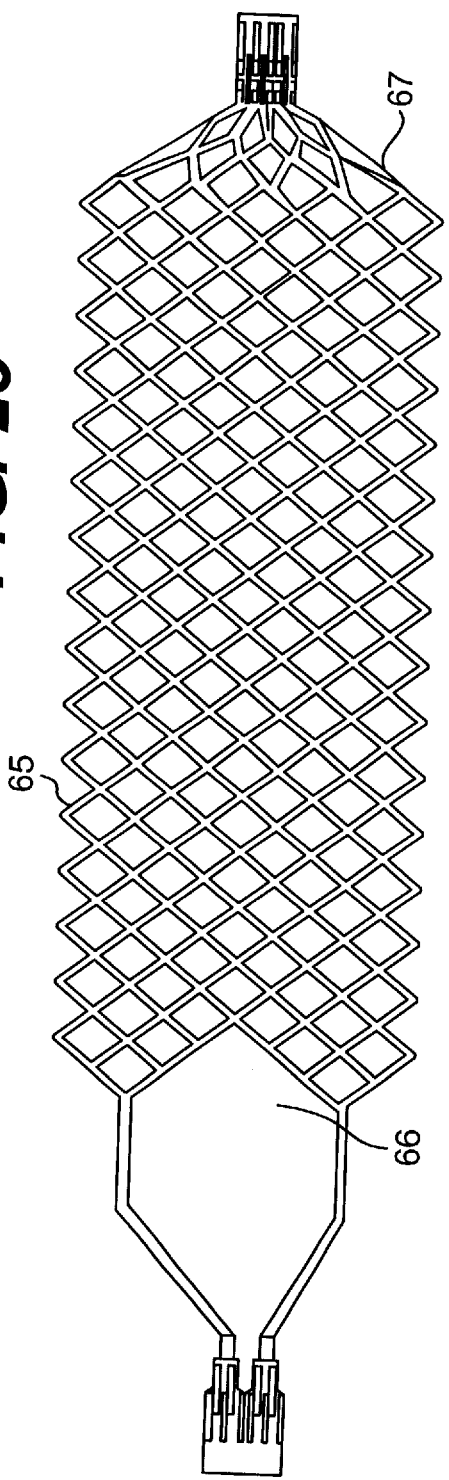

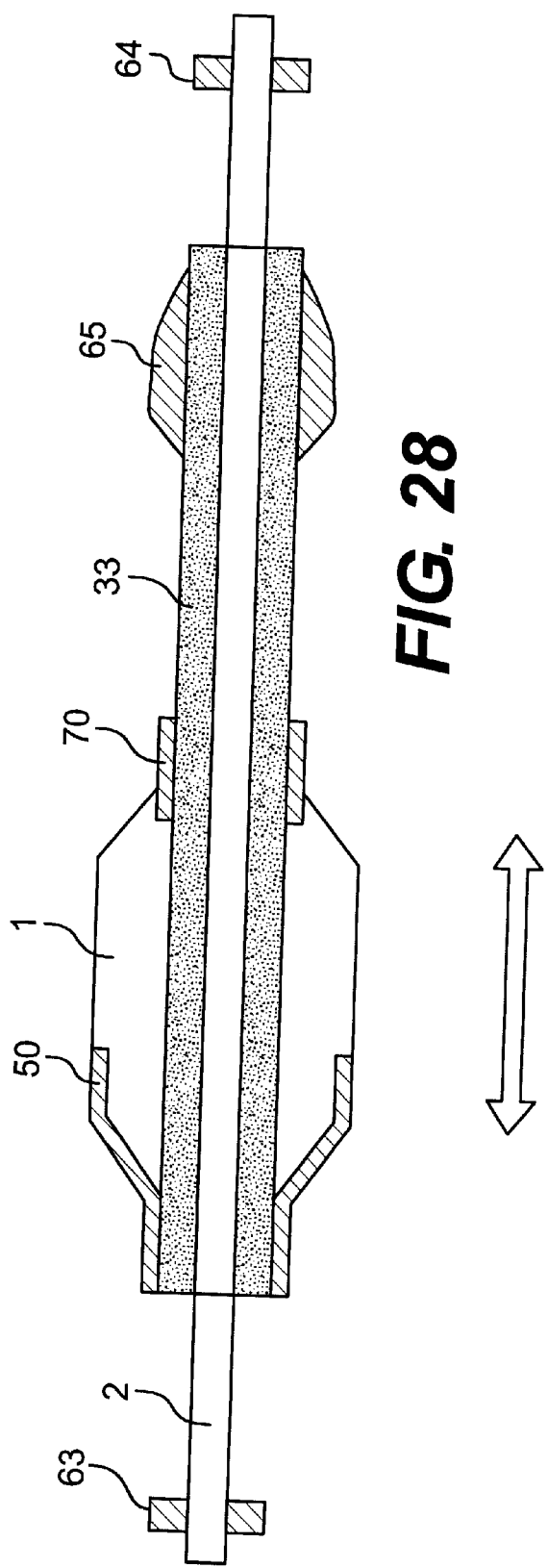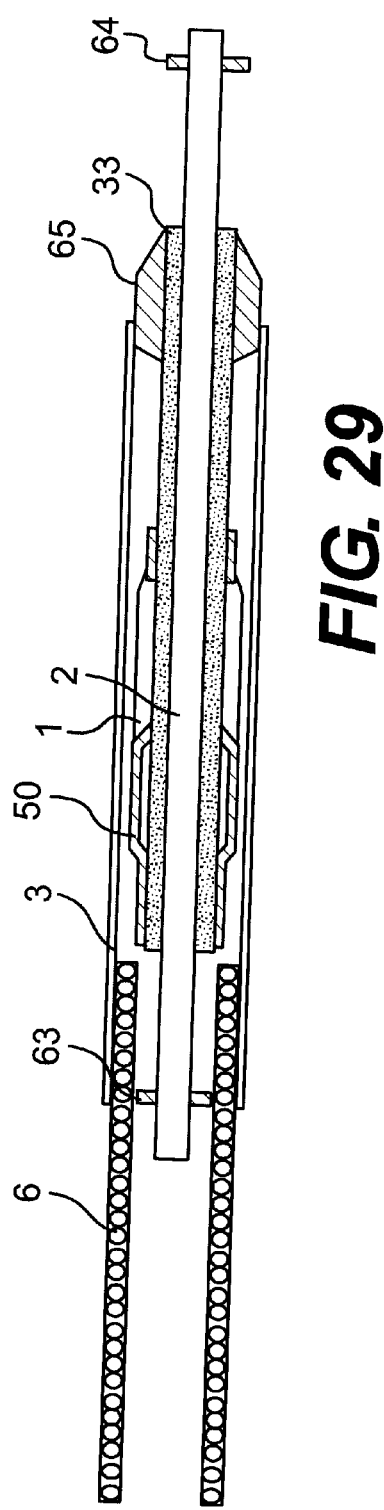

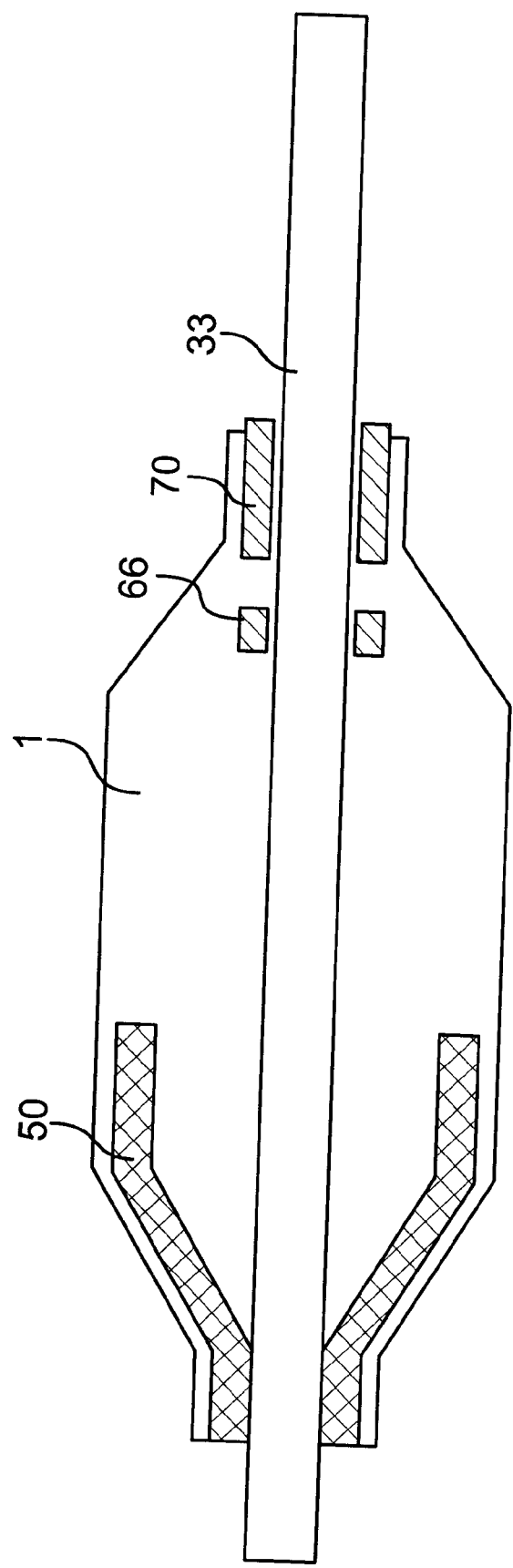

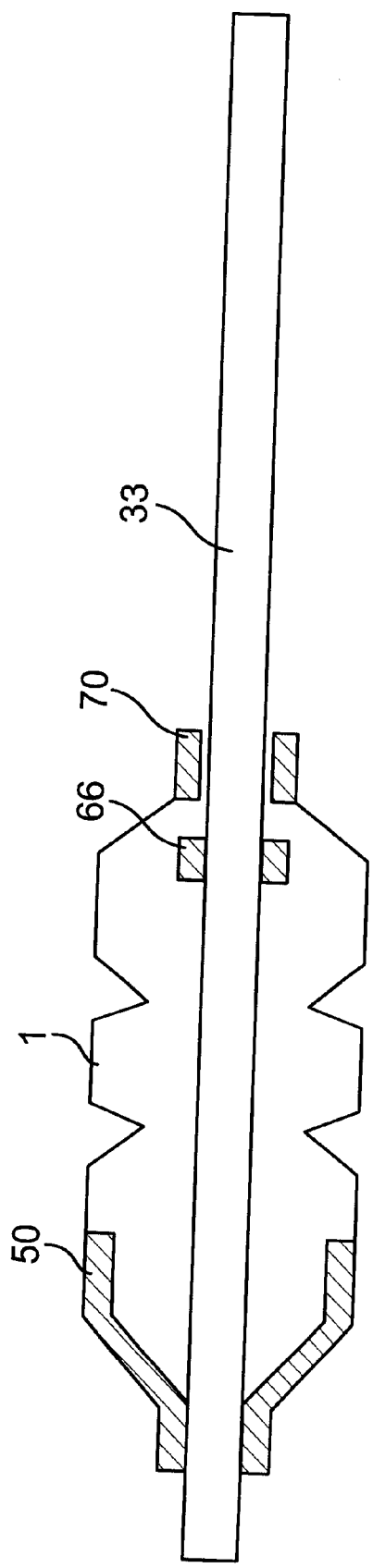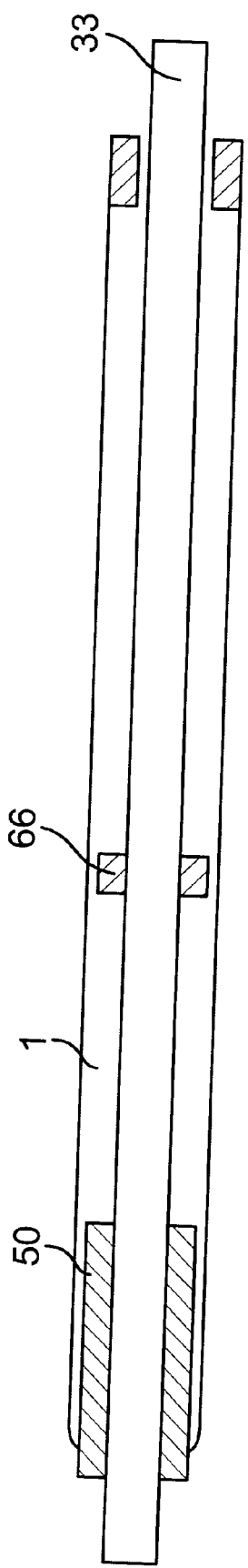
FIG. 33a
FIG. 33b

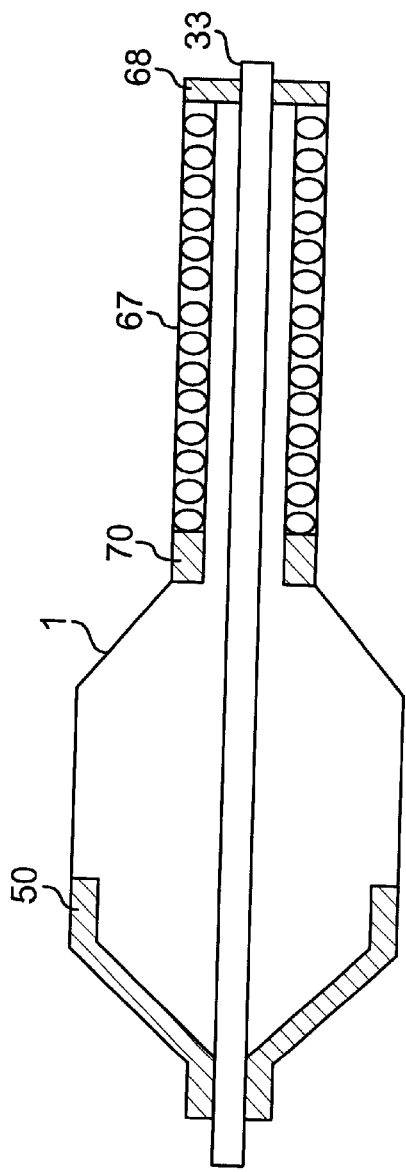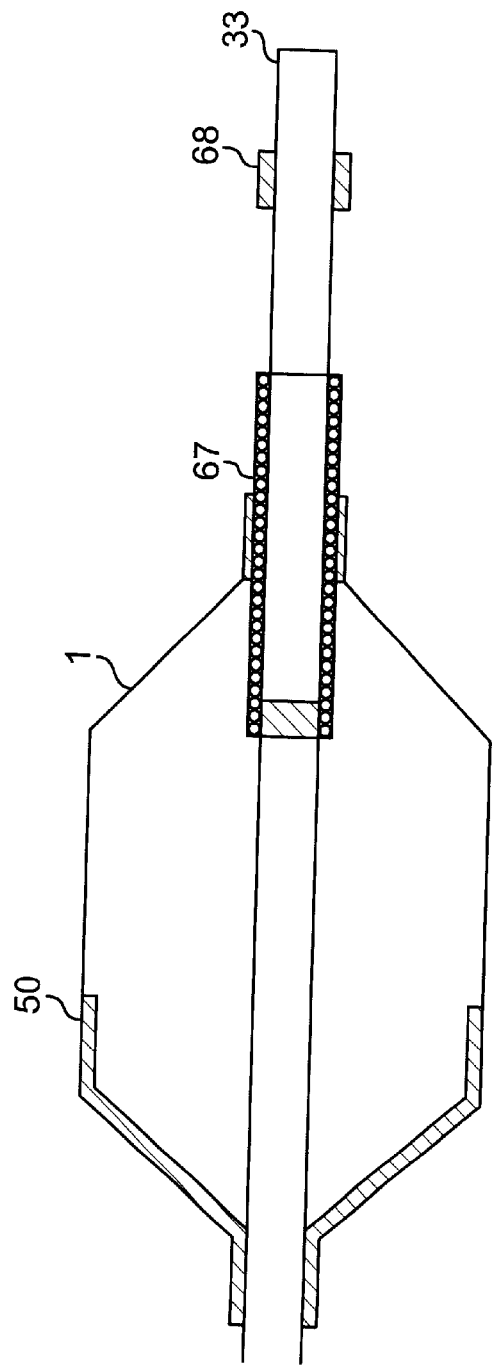

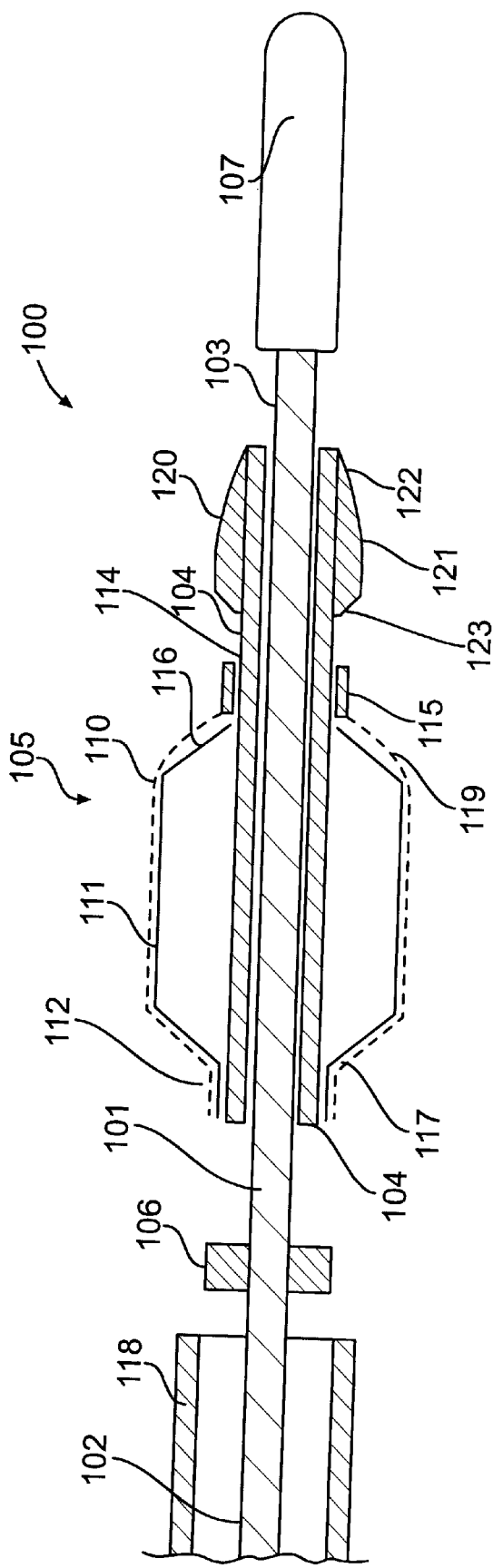
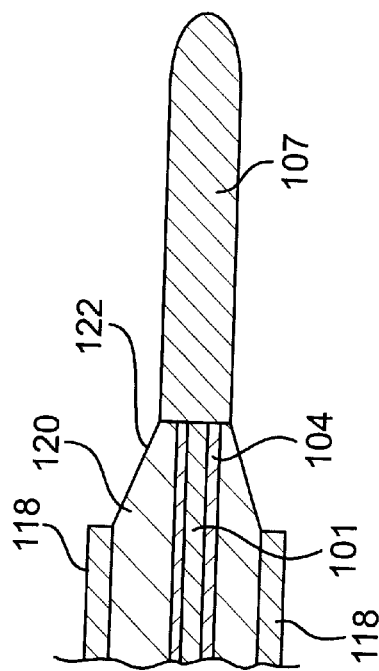
FIG. 41
FIG. 42

EMBOLIC PROTECTION DEVICE

INTRODUCTION

The invention relates to an embolic protection device.

The term "STROKE" is used to describe a medical event whereby blood supply to the brain or specific areas of the brain is restricted or blocked to the extent that the supply is inadequate to provide the required flow of oxygenated blood to maintain function. The brain will be impaired either temporarily or permanently, with the patient experiencing a loss of function such as sight, speech or control of limbs. There are two distinct types of stroke, haemorrhagic and embolic. This invention addresses embolic stroke.

Medical literature describes carotid artery disease as a significant source of embolic material. Typically, an atherosclerotic plaque builds up in the carotid arteries. The nature of the plaque varies considerably, but in a significant number of cases pieces of the plaque can break away and flow distally and block bloodflow to specific areas of the brain and cause neurological impairment. Treatment of the disease is classically by way of surgical carotid endarterectomy whereby, the carotid artery is cut and the plaque is physically removed from the vessel. The procedure has broad acceptance with neurological complication rates quoted as being low, somewhere in the order of 6% although claims vary widely on this.

Not all patients are candidates for surgery. A number of reasons may exist such that the patients could not tolerate surgical intervention. In these cases and an increasing number of candidates that are surgical candidates are being treated using transcatheter techniques. In this case, the evolving approach uses devices inserted in the femoral artery and manipulated to the site of the stenosis. A balloon angioplasty catheter is inflated to open the artery and an intravascular stent is sometimes deployed at the site of the stenosis. The action of these devices as with surgery can dislodge embolic material which will flow with the arterial blood and if large enough, eventually block a blood vessel and cause a stroke.

It is known to permanently implant a filter in human vasculature to catch embolic material. It is also known to use a removable filter for this purpose. Such removable filters typically comprise umbrella type filters comprising a filter membrane supported on a collapsible frame on a guidewire for movement of the filter membrane between a collapsed position against the guidewire and a laterally extending position occluding a vessel. Examples of such filters are shown in U.S. Pat. No. 4,723,549, U.S. Pat. No. 5,053,008, U.S. Pat. No. 5,108,419 and WO 98/33443. Various deployment and/or collapsing arrangements are provided for the umbrella filter. However, as the filter collapses, the captured embolic material tends to be squeezed outwardly towards an open end of the filter and pieces of embolic material may escape from the filter with potentially catastrophic results. More usually, the filter umbrella is collapsed against the guidewire before removal through a catheter or the like. Again, as the filter membrane is collapsed, it will tend to squeeze out the embolic material. Further, the umbrella filter is generally fixed to the guidewire and any inadvertent movement of the guidewire during an interventional procedure can dislodge the filter.

The present invention is directed towards overcoming these problems.

There is a need for an embolic protection device which will overcome this problem.

STATEMENTS OF INVENTION

According to the invention, there is provided an embolic protection device comprising:

a collapsible filter element mounted on a filter carrier for delivery through a vascular system of a patient, the filter element being movable between a collapsed stored position against the filter carrier for movement through the vascular system, and an expanded position for occluding a blood vessel such that blood passing through the blood vessel is delivered through the filter element, the filter element comprising a collapsible filter body having an inlet end and an outlet end, the inlet end of the filter body having one or more inlet openings sized to allow blood and embolic material enter the filter body, the outlet end of the filter body having a plurality of outlet openings sized to allow through passage of blood but to retain undesired embolic material within the filter body, means for closing the inlet openings at the inlet end of the filter body, and means for collapsing the filter body on the support.

Advantageously, the inlet openings in the filter are closed before the filter is collapsed ensuring retention of all embolic material within the filter element.

In a particularly preferred embodiment of the invention, the means for closing the inlet comprises:

a tubular filter retrieval device having an open distal end for reception of the filter element, said distal end being engagable with a proximal inlet end of the filter body to close the inlet openings and being slidable over the filter body from the inlet end to the outlet end to progressively collapse the filter body on the filter carrier and receive the filter body within the retrieval device.

Conveniently, the retrieval device which may be a catheter or pod or the like which engages and collapses the filter element firstly closing the inlet openings to prevent any escape of embolic material and then collapsing the remainder of the filter, being slid from the proximal end over the filter to the distal end of the filter.

In a particularly preferred embodiment, the collapsible filter element is slidably mounted on the filter carrier between the a pair of spaced-apart stops on the filter carrier for axial movement of the filter element along the filter carrier between the stops.

Advantageously, the filter carrier which may for example be a guidewire can be moved independently of the filter element and thus accidental movement of the guidewire is accommodated without unintentionally moving the filter, for example, during exchange of medical devices.

In a further embodiment, the filter element is rotatably mounted on the filter carrier.

In a preferred embodiment, a sleeve is slidably mounted on the filter carrier between the stops, the length of the sleeve being less than the distance between the stops, the filter element being mounted on the sleeve.

In a particularly preferred embodiment, the filter element comprises:

a collapsible filter net mounted on the filter carrier, the filter net being movable between a collapsed stored position against the filter carrier and an expanded position extending outwardly of the filter carrier for deployment across a blood vessel.

Preferably, the tubular filter retrieval device comprises a catheter slidable along the filter carrier, an open distal end of the catheter forming a housing for reception of the filter element.

In another embodiment, a proximal inlet end of the filter body is fixed to the filter carrier and a distal end of the filter body is slidably mounted on the filter carrier, although this arrangement may be reversed.

In a further embodiment, the distal end of the filter body is attached to a collar which is slidable along the filter carrier.

In a preferred embodiment, a filter support frame is mounted on the filter carrier, the support frame being movable between a collapsed position along the filter carrier and an extended outwardly projecting position to support the filter body in the expanded position.

In another embodiment, the filter support frame is fixed on the filter carrier at a proximal end of the filter body.

Preferably, the filter support frame slidably engages the filter carrier at a distal end of the filter body. Ideally, the filter support frame is biased into a normally extended position.

In a further embodiment, a circumferential groove is provided in the filter body intermediate the ends of the filter body.

In another embodiment, a guide olive is provided on the filter carrier distally of the filter body, the guide olive having a cylindrical body with a tapered distal end, the cylindrical body being engagable within a distal end of a deployment catheter, said tapered distal end projecting outwardly of the deployment catheter to provide a smooth transition between the catheter and the filter carrier.

In a further embodiment, the net is gathered into the filter carrier at each end of the net.

In another embodiment of the invention, there is provided an embolic protection device comprising a filter element for placing in a desired position, the filter element providing a pathway for blood and having means for capturing, retaining and removing undesired embolic material.

In one embodiment of the invention, the pathway has means for constricting flow to capture undesired embolic material.

In another embodiment of the invention, the filter has a proximal end and a distal end, openings in the proximal end being larger than openings in the distal end, the proximal end openings being sized to allow the flow of blood and embolic material to enter the filter element and the distal end openings being sized to allow the flow of blood while capturing undesired emboli within the filter element.

In a further embodiment of the invention, the filter element includes storage means to store captured undesired embolic material in the filter element. Preferably, the storage means comprises additional storage pathways within the filter element. Preferably, the filter element defines a three dimensional matrix.

In another embodiment of the invention, the filter element is of a polymeric porous structure. In a further embodiment of the invention, the matrix comprises a porous structure dimensioned to entrap embolic material which typically ranges in size from about 100 microns to 3500 microns. In a still further embodiment of the invention, the filter element is compressible and/or foldable for loading into a delivery device to deliver the filter element to a desired location in the compressed or folded state.

In one embodiment of the invention, the filter element has material removed from its structure to aid compressibility.

In another embodiment of the invention, the filter element has material removed from its structure to provide specific sizing in relation to the size of embolic material to be trapped.

In a further embodiment of the invention, the filter element has pathways through the filter body that are interlinked such that the flow rate through the filter may be tailored.

In another embodiment of the invention, the filter element has a distal end which is tapered such that there is a smooth transition in lateral stiffness to improve the manoeuvrability of the filter element in the vascular system.

In a further embodiment of the invention, the filter element has a soft distal portion to aid in atraumatic transport through the vascular system. Preferably, the filter element has circumferential grooves to reduce the lateral flexibility of the filter element.

In one embodiment of the invention, the filter element has a tapered proximal end to facilitate retrieval by a removal catheter.

In another embodiment of the invention, the filter element has inlet holes that close on pulling back into a retrieval catheter to ensure retention of any collected emboli.

In a further embodiment of the invention, the filter element has outlet openings sized to capture embolic material of a size large enough to impair the function of the organ receiving the blood downstream of the filter body element. Preferably, the filter element is sized to capture embolic material of a size greater than 100 microns. Most preferably, the filter element is sized to capture embolic material of a size greater than 200 microns. Most preferably, the filter element is sized to capture embolic material of a size greater than 500 microns.

In one embodiment of the invention, the filter element is sized for complete coverage of a vessel cross-section that allows passage of blood and blood components.

In a still further embodiment of the invention, there is provided a device having means for placing over a medical guidewire.

In another embodiment of the invention, there is provided a device which may be placed under a balloon or stent delivery catheter.

In a further embodiment of the invention, there is provided a device having means for insertion through, femoral, brachial, radial, subclavian or other arterial puncture by means of a transcatheter approach.

In one embodiment of the invention, there is provided a device for protection of neurological function which is inserted for the duration of a surgical intervention at or near the site of surgical opening.

It is envisaged that two devices could be used bi-laterally in left and right carotid arteries allowing sufficient cerebral blood flow to maintain neurological function during procedures with a high risk of generating clot such as electrophysiological treatment of coronary arrhythmias.

In a further embodiment of the invention, there is provided a device including a delivery catheter in which an external sheath is engagable with the filter element or filter carrier to provide push during delivery and is removable to allow maximum space in the vascular cross-section during an interventional procedure.

In one embodiment of the invention, the external sheath is joined to the filter element or filter carrier by a joining means. The joining means may be a removable shrink tube or a removable clip. Preferably the joining means is a compression connector such as a Tuohy Borst adapter.

In another embodiment of the invention, the delivery catheter has a central lumen for at least part of it's length to allow it to track over a steerable guidewire.

In a further embodiment of the invention, the external sheath is sufficiently long to extend to the outside of the vasculature and is movable proximally to release the filter element from the catheter.

In one embodiment of the invention, the delivery catheter has an external covering which extends beyond the push element to define a filter retention sleeve.

In another embodiment of the invention, the delivery catheter has a spring component with a localised stepwise increasing pitch to alter stiffness characteristics to suit the target vasculature.

In a further embodiment of the invention, the delivery catheter has a spring component with a localised gradually increasing pitch to alter stiffness characteristics to suit the target vasculature.

In one embodiment of the invention, the filter element is mounted on a collapsible support structure which is movable between a collapsed position for deployment and an extended in-use position, means being provided for retaining the support structure in the collapsed position. Preferably, the support structure comprises support arms. Preferably, the support arms are formed from a shape memory or elastic memory material. Most preferably, the support arms are formed from Nitinol.

In one embodiment of the invention, the support arms are configured to open co-axially with the filter carrier such that they may be restrained for removal by pulling the filter element proximally into an appropriately dimensioned sheath.

In another embodiment of the invention, the filter element has an associated support structure with a pre-shaped spiral arrangement such that it provides radial support to the filter element.

In a further embodiment of the invention, the filter support structure is adapted to fold into the collapsed position when pulled into a retrieval catheter.

In one embodiment of the invention, the filter element comprises a flexible shaped polymeric component.

In another embodiment of the invention, the shaped polymeric component is constructed such that fluid flow through the component assists in opening the component from the collapsed position.

In a further embodiment of the invention, the shaped polymeric component is flexible and opens to make cicumferential contact with the vessel wall by way of using the pressure drop across the exit filter face.

In a further embodiment of the invention the filter element is mounted on a guidewire such that the guidewire has freedom to rotate and/or move axially independently of the filter. More preferably the wire has complete freedom to rotate independently of the filter and has limited axial movement. The limit of axial movement is determined by stops mounted on or connected to the wire. Ideally the wire can move 100 mm in the axial direction independent of the filter. More ideally the wire can move less than 50 mm independently of the filter. This embodiment facilitates the maintenance of filter position during the exchange of catheters and permits the steering of the wire independent of the filter.

In a further embodiment of this invention the filter element is bonded to the filter mount at its proximal end and its distal end is free to move relative to the filter mount and proximal bond so as to aid the collapse of the filter for deployment.

In a further embodiment of the invention the filter element is tapered over part or all of its length such that it is accurately sized to the vessel over some portion of its length.

In a further embodiment of the invention the shaped polymeric component contains one or more circumferential grooves along its body to maintain the circular shape of the filter element in an under sized artery.

In one embodiment of the invention, the filter element is directly bonded onto a steerable medical guide wire incorporating a slidable sheath that is movable to deploy the filter.

In another embodiment of the invention, there is provided a device incorporating a medical guidewire with a flexible segment of wire distal to the filter so as to provide steerability of the wire particularly prior to it being deployed.

In a further embodiment of the invention, there is provided a device incorporating a medical guide wire with a soft distal segment so as to provide a tip section that will be atraumatic.

In a still further embodiment of the invention, there is provided a device with a porous coating on a distal end of the filter element only with a means for opening and closing the filter by slidable motion.

In one embodiment of the invention, the filter element incorporates proximal tapering such that it may be pulled proximally into a sheath for removal in order that such pulling action will effectively reduce the diameter of the filter and assist retrieval.

In another embodiment of the invention, the filter element has a porous structure that can be deployed and closed by way of a slidable motion, the closure thereof caused by way of snap-fit to a protruding rim that allows the support elements be pulled proximally, thus closing the structure with the filter membrane attached.

In a further embodiment of the invention, there is provided a device having a filter element which permits the incorporation of a medical guide wire in the outer wall of the filter element to facilitate the incorporation of large inlet holes on the proximal inlet end of the filter element.

In one embodiment of the invention, the filter element comprises a mesh work structure with large proximal inlet holes and small distal outlet holes wherein the mesh structure is collapsible into a small diameter delivery catheter and is expandable upon deployment to a shape which is remembered by the mesh structure either through shape memory characteristics or elastic memory characteristics.

In another embodiment of the invention, the filter element comprises a mesh work structure wherein the expansion of the filter element within the vessel causes blood flowing through the vessel to flow through the filter element due to the filter element engaging with the wall of the vessel to conform to the shape of the vessel bore.

In another embodiment, the filter element comprises a braided fibrous mesh work. Preferably, distal outlet openings are defined by an area enclosed by a series of crossing interwoven fibres. Larger proximal inlet holes are provided by the convergence of the fibres of the braid into a few bundles which are mounted to the filter carrier. Preferably, the fibrous meshwork material is an elastic or shape memory material such that it can be collapsed into a delivery catheter and recover its enlarged shape upon deployment. The fibres of the meshwork are bonded at the points where they cross one another. The fibres may be made from either a polymer or metal or a composite material.

In a further embodiment, the distal end of the filter element has the facility to move in the axial direction relative to the proximal end of the filter element so as to take up the exact shape of the blood vessel.

In a further embodiment, the device has a porous coating on a distal end of the filter element only with means for opening and closing the filter element by slidable motion. Preferably, the filter element comprises a collapsible wire frame having a plurality of wires, outer ends of the wires being hingedly mounted on the filter carrier, the wires being hinged intermediate their ends, at one end the wires being fixed on the filter carrier and at the other end the wires being mounted on a collar which is slidable along the filter carrier, a porous filter mesh being mounted on the wire frame. An actuating sleeve is slidable over the filter carrier to push the collar towards the fixed end of the filter element, and a collapsing device is engagable with the collar to pull back the collar away from the fixed end of the filter element to collapse the wire frame against the filter carrier for retrieval of the filter element.

In a still further embodiment of the invention, there is provided a filter retrieval system for use with the device comprising a longitudinal catheter with a radially deformable or elastic tip to assist the pull back of the filter into the tip.

In another embodiment of the invention, there is provided a system incorporating a filter, a delivery catheter and a retrieval catheter for temporary filtration of the vascular system during an interventional procedure.

In another aspect the invention provides an embolic protection device comprising:

a collapsible filter element mounted on a filter carrier for delivery through a vascular system of a patient, the filter element being movable between a collapsed stored position against the filter carrier for movement through the vascular system, and an expanded position for occluding a blood vessel such that blood passing through the blood vessel is delivered through the filter element, a pair of spaced-apart stops on the filter carrier, the collapsible filter element being slidably mounted on the filter carrier for axial movement along the filter carrier between the stops, and means for collapsing the filter element on the filter carrier.

BRIEF DESCRIPTION OF DRAWINGS

The invention will be more clearly understood from the following description thereof given by way of example only with reference to the accompanying drawings in which:

FIG. 3A is a side view illustrating one method of fixing the device to catheter;

FIG. 3B is a side view of an embolic protection device incorporating the fixing of FIG. 3A;

FIG. 4 is a side view illustrating another method of fixing;

FIG. 5 is an end view of a split collar used in the fixing of FIG. 4;

FIG. 8 is a side view of one filter element used in the device of the invention;

FIG. 9 is a side view of another filter element;

FIG. 11 is an isometric view of another filter element in an in-use placed configuration;

FIG. 12 is a side view of the filter element of FIG. 11 in a retracted position for insertion and withdrawal;

FIGS. 16 and 17 are side views of part of a further filter element with a snap fit retrieval arrangement;

FIG. 18 is a perspective, partially cross-sectional view of another embolic protection device shown mounted in a vessel;

FIGS. 19a to 19c are perspective views illustrating the formation of a collapsible filter support for use in the device of FIG. 18;

FIGS. 20 to 22 are perspective views of other filter elements;

FIG. 23 is an elevational view of another filter element;

FIG. 24 is a sectional view taken along the line XXIV—XXIV of FIG. 23;

FIG. 25 is a sectional view taken along the line XXV—XXV of FIG. 23;

FIG. 26 is an enlarged detail view of portion of the filter;

FIG. 27 is an expanded view of the filter element of FIG. 23;

FIG. 28 is a side view illustrating one method in which the substrate tubing that the filter element is attached to can run over the primary crossing guidewire;

FIG. 29 is a side view illustrating the position in which the "olive" component will sit in order to provide a smooth transition between the primary crossing guidewire and the loading pod;

FIG. 32 is a perspective view of the filter element when the distal end of the filter is not bonded to the substrate tubing;

FIG. 33 is a side view of a concertina shaped filter; A being when the filter is deployed and B when the filter is in its loaded shape;

FIG. 34 is a perspective view of the floating detail tip design with a spring element incorporated distal to the floating tip;

FIG. 35 is a side view of another floating distal tip design with a spring incorporated into the distal tip;

FIG. 41 is a schematic sectional elevational view of the embolic protection device of FIG. 40; and FIG. 42 is a detail sectional view of portion of the device of FIG. 40.

DETAILED DESCRIPTION

Figure 1:
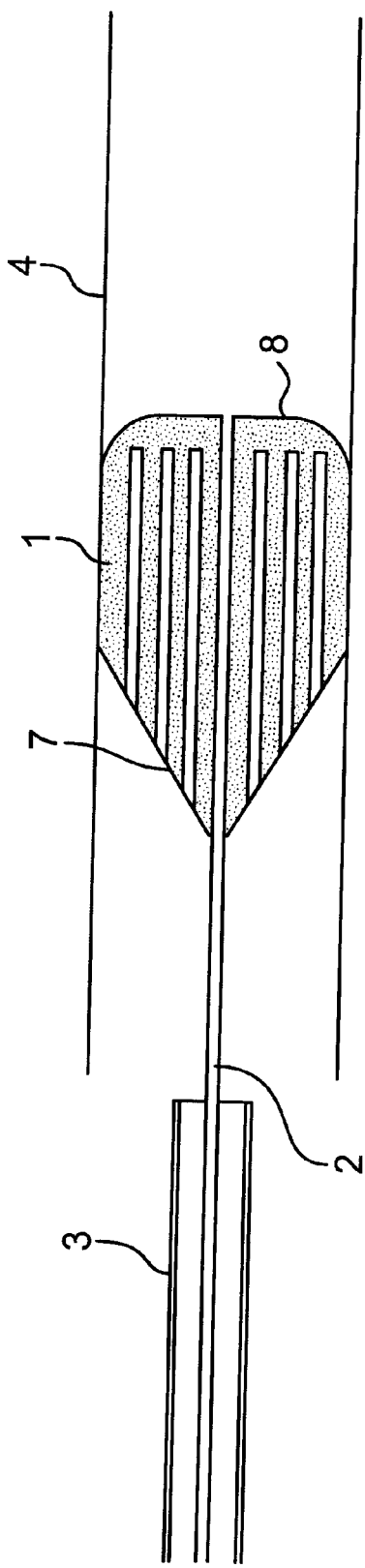
FIG. 1 is a side view of an embolic protection device according to the invention, in use.

Referring to the drawings there are illustrated various embolic protection devices according to the invention. The devices, in general, comprise a filter element for temporary placing in a desired position during a surgical or interventional procedure, typically using a guidewire and catheter. The filter element provides a pathway for blood and has means for capturing and retaining undesired embolic material released during the surgical procedure. The filter element containing the retained embolic material is removed when the interventional procedure is completed. In this way the patient is protected against the risk of stroke or other complications caused by the release of undesired embolic material during the procedure.

In one embodiment of the device it will be used in an over the wire transcatheter configuration. The clinician will cross the lesion with a steerable guidewire. The cerebral protection device will then be threaded over the guidewire and will be placed distal to the site of the lesion being treated. By means of actuation, or other means, the filter is deployed into the vessel and will capture emboli that are generated or dislodged during balloon inflation and stent placement. The device consists of a filter attached to a shaft than can run over the primary crossing guidewire.

Figure 2:
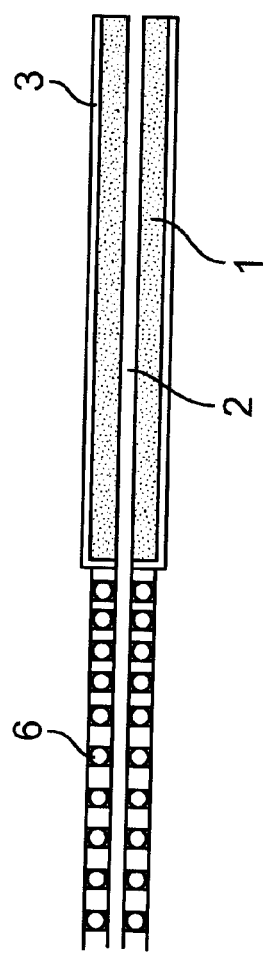
FIG. 2 is a side view of the device of FIG. 1 in a pre-loaded position for insertion.

Referring initially to FIGS. 1 and 2 in this case the filter element consists of a compressible porous structure polymeric foam filter element 1 overmoulded onto or joined to a polymeric or metallic tube or spring or other hollow support element 2. The foam filter element 1 is compressed into a housing or pod 3 at a distal end of a catheter 6 to advance it to the required location. Once in situ the housing 3 is withdrawn or the filter element 1 is advanced. This action allows the compressed filter element 1 to expand to the required size and occlude a blood vessel 4 except for the path or paths provided through the filter element 1. The filter element 1 is designed to provide a pathway or multiple pathways through for blood cells and other blood constituents but to capture emboli of a size greater than the filter pore size. Blood flow rate is maintained by forming the filter element such that a local pressure drop across the filter is minimised. The filter element 1 has a proximal inlet end 7 and a distal outlet end 8. The inlet end 7 has a plurality of inlet openings sized to allow blood and embolic material enter the filter element. The outlet end 8 has a plurality of outlet openings sized to allow through passage of blood but to retain undesired embolic material within the body of the filter element 1.

The filter element 1 in this case is of a porous structure or polymeric foam which has a open cell structure with a typical density less than 400 kg per cubic meter. Preferably the density will be less than 100 kg per cubic meter and ideally will be less than 50 kg per cubic meter. The filter properties may be achieved through appropriately sizing the pores of the foam body or additionally by removing material to create appropriately sized pathways for blood to flow through and means of capturing larger sized particles. A number of configurations for this will be described that can tailor both the sizing and flow rate characteristics of the filter element 1 either independently or simultaneously. The actuation and deployment of the filter element 1 are achieved by providing relative motion between the filter element 1 and the covering housing 3.

It is not desirable that the catheter moves relative to the support element 2 during manipulation. Motion may be prevented by fixing the inner support element 2 to the catheter 6 in a number of different ways. In the embodiment described this is achieved by way of having a catheter 6 covering the support element 2 and filter element 1 to which it is fixed. As illustrated in FIGS. 3A and 3B the fixing may be achieved by means of a shrink wrap tube 5 that is shrunk to capture both the covering catheter 6 and the inner support element 2. Once the filter element 1 is in the desired position, the shrink-wrap joint is broken using the peel-away tab 7 to allow the outer catheter 6 to be removed proximally and leave the support element 2 and filter element 1 in place.

Figure 6:
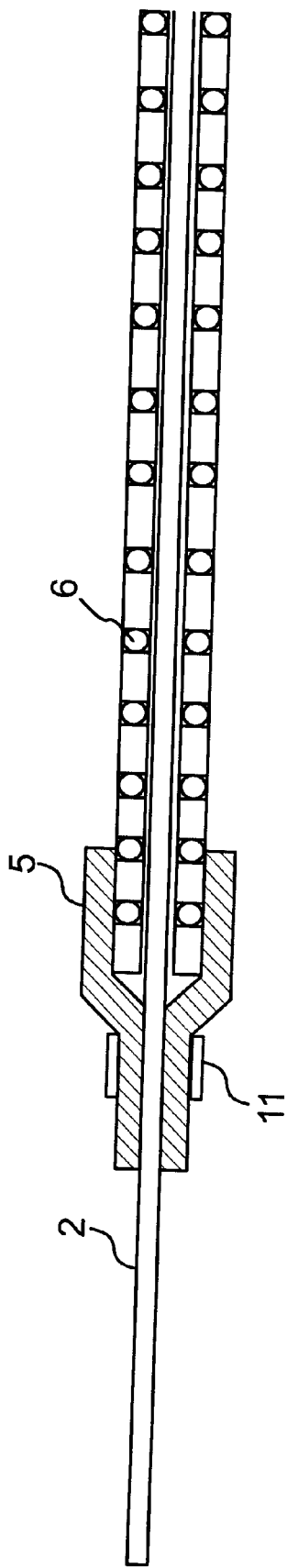
FIG. 6 is a side view illustrating a further method of fixing.
Figure 7:
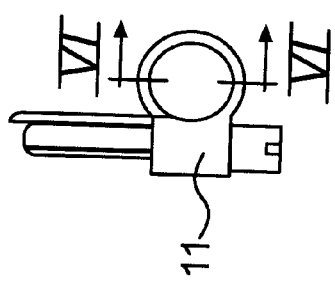
FIG. 7 is an end view of a jubilee clip used in the fixing of FIG. 6.

A number of other workable arrangements could be used to join the support element 2 and catheter 6. A split collar arrangement 10 (FIGS. 4 & 5) could be used that was removable by means of unlocking a screw or a number of screws or an arrangement such as a jubilee clip 11 (FIGS. 6 & 7) which could be loosened to free the bond between the components.

Another method that could be used to temporarily fix the inner support element 2 to the outer sheath or catheter 6 is a Hemostasis High Pressure Touhy Borst Y adapter. This commercially available adapter is needed to enable the physician to flush the sheath before being inserted into the artery. The outer sheath or catheter may be permanently attached to this adapter. The inner tubular support element 2 runs through the Touhy Borst section of the adapter and thus through the centre of the sheath. Tightening the Touhy Borst section releases this grip, thus allowing the inner tubular support element 2 and the outer sheath to move relative to each other once again.

The design of the filter element 1 is shown in a typical embodiment in FIG. 8, where a foam substrate filter body has material removed to create a series of channels or pathways 20 for the blood to flow through but which would cause a restriction for embolic material to prevent it going through the filter. The pathways 20 may be machined using a variety of methods such as laser cutting with excimer, YAG, CO2, or other laser type, freezing and machining or lost wax machining. A number of arrangements are possible with the sizing reflective of the requirements. In the configuration shown, the inlet holes are preferably 0.5 mm or greater in size to capture large emboli while the outlet holes are less than 300 microns. These can be easily varied as required to filter differing sized particles from a variety of fluid media in a variety of vessel sizes.

The filter media can be bonded to the tubing substrate by way of a variety of available technologies such as mechanical, solvent or adhesive bonding and overmoulding in an arrangement such that the substrate is placed in the mould and the polymer material is then shot into the mould and forms a bond at the interface between the substrate and the polymer element. Additionally, the foam or porous element could be extruded onto or bonded to a substrate.

It will be noted that the filter element 1 has a rounded distal end 21 to facilitate insertion and the proximal end 22 is tapered to facilitate withdrawal. Alternatively, as illustrated in FIG. 9 the distal end 23 may be tapered.

Figure 10:
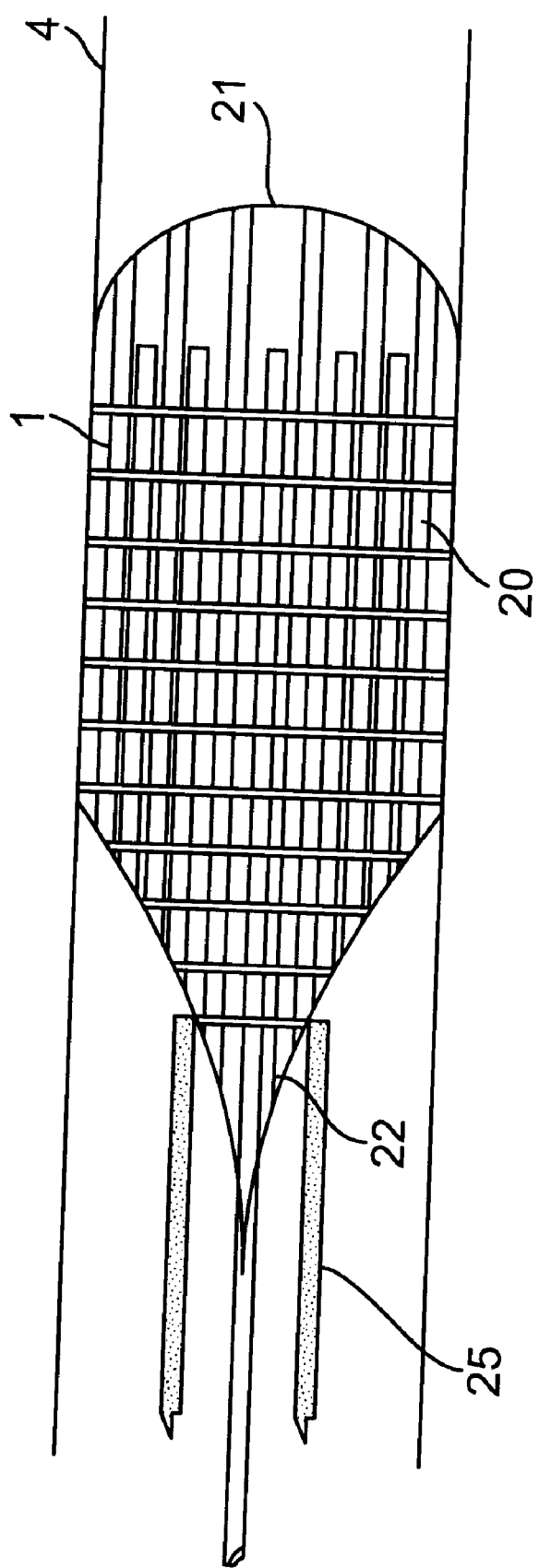
FIG. 10 is a side view of the filter element of FIG. 8 being removed.
Figure 13:
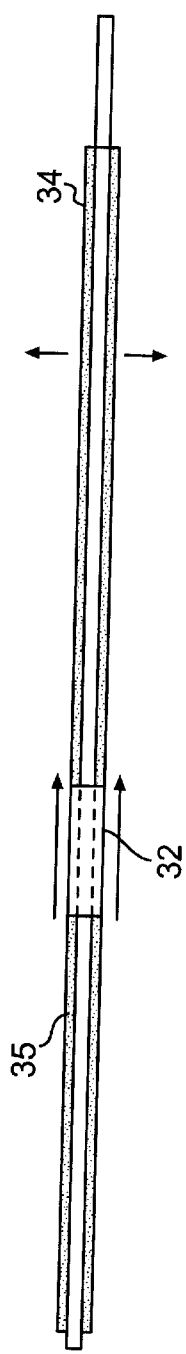
FIGS. 13 to 15 are side views of another filter element in different positions.
Figure 14:
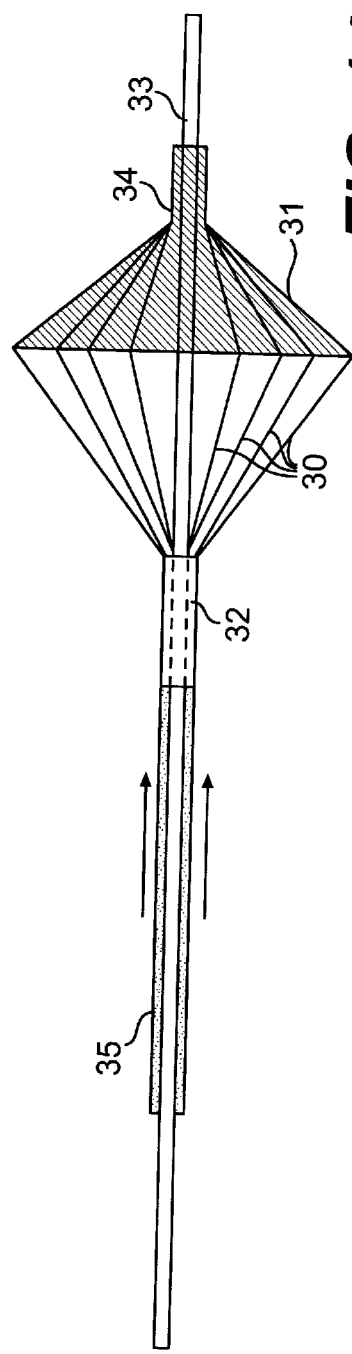
Figure 15:
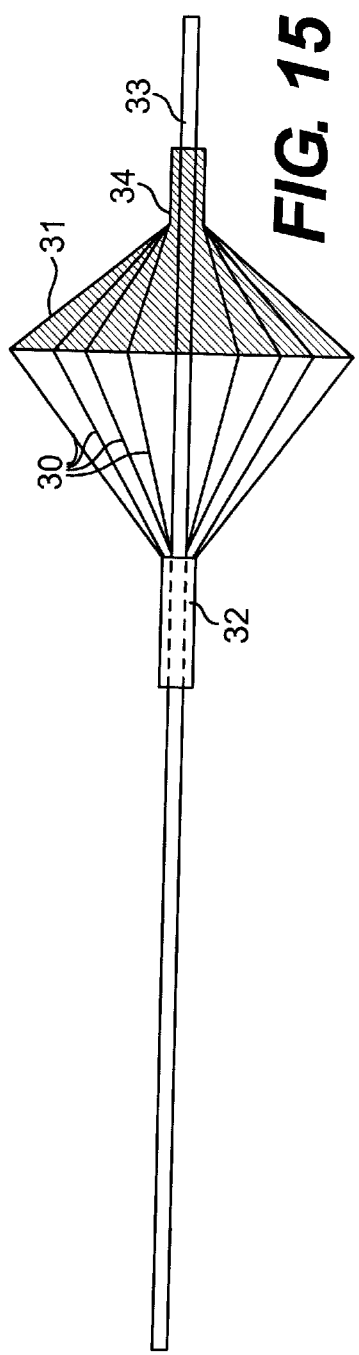

Referring particularly to FIG. 10 at the end of the interventional procedure, the device can be withdrawn by means of advancing a large bore catheter 25 to the proximal end 22 of the filter 1 and pulling the filter 1 into the catheter 25. The filter 1 will compress and seal the proximal filter inlet openings after the initial taper is drawn into the catheter 25 before collapsing the rest of the filter body. Once the filter 1 has been withdrawn fully into the catheter 25 it can then be readily removed from the patient. The filter 1 will contain the captured emboli.

In another embodiment of the invention as illustrated in FIGS. 11 to 15, an arrangement of spokes 30 covered with a membrane or porous fabric or mesh 31 can be folded down into a delivery sheath or pod for subsequent deployment in the target vessel. The design consists of a substrate shaft 33 onto which are radially or circumferentially bonded a series of pre-shaped wires 30. The wires 30 are joined on the proximal end into a movable collar or tube 32 mounted on the substrate shaft 33 and at the distal end into a fixed tube 34. The tube 32 can move proximally and distally to the extent that it will open and close the assembly in a manner similar to an umbrella and thereby occlude the vessel. The spokes 30 may be fabricated in a range of metallic, polymeric and composite materials. The frame is covered with a porous material 31, whose pore size is selected to allow the media through, effectively creating a screen filter. The covering fabric 31 could be bonded to the frame 30 by means of casting a material such as a polyurethane or PET onto the pre-formed shape. The film may then be lazed or made porous by other means such as mechanical or heat punching or by chemical etching. Additionally, incorporating a soluble particle in the polymer matrix, subsequent removal of the particle would render the polymer porous. Control of porosity is achieved by tailoring the ratio and distribution of the particulate within the polymer matrix.

When the assembly is configured longitudinally a sheath or pod may be slid over it to cover it. As with the previous embodiment, the loaded catheter is positioned in the required location by threading it over the guidewire. Once the desired location has been reached, the sheath may be moved back and allow the assembly be exposed in the vessel. A sleeve 35 can then be moved forward to open or deploy the assembly. The relative sizing and choice of materials operates such that the sleeve 35 will not slide on the inner tubing unless an external force is applied to move it. When deployed, the device will remain open and catch whatever embolic material is moving towards the brain. At the end of the procedure, a pre-shaped component advanced over the inner tube will dock with the movable tube 32 and allow it to be slid towards the proximal end of the device with the result that the structure is closed. A larger sheath can then separately be advanced to the site of the filter and the filter may be pulled or manipulated proximally into it. When withdrawn into the sheath or catheter, the device may then be removed either over the guidewire or with it.

Referring to FIGS. 16 and 17 there is illustrated another embolic protection device. In this case the filter element has a design based on a shaped thin film component bonded onto the tubing substrate. A wide number of shapes could be made to work in the application. An element which through it's preshaped form will open into a framework 40 when the restraining force is removed is attached to a tubing substrate 41. The frame element 40 can be manufactured from a range of metallic or polymeric components such as a shape memory alloy like Nitinol or a shape memory polymer or a shaped stainless steel or metal with similar properties that will recover from deformation sufficiently to cause the film component to open. Otherwise a mechanical movement or actuation can cause the device to open. The shaped film component is attached over the frame 40. The film component can be formed by a number of known commercial technologies. These include blow-moulding, dip casting, solution casting, spin casting and film welding as well as adhesive joining. The object is to produce a formed shape that can be opened in the vessel to a size and shape to occlude it. Filtration is achieved by creating a pattern or series of openings in the proximal and distal ends of the element that allows emboli and blood to enter the device but having a range of smaller openings in the distal end to allow the blood to pass through to the distal vasculature while retaining the emboli.

While being delivered to the required site, the filter element is covered or restrained by a sheath. By withdrawing the sheath or advancing the filter device, the filter is uncovered and opens to occlude the vessel. During the procedure, the filter acts to capture all embolic material that attempts to flow distally. At the end of the procedure, a sheath is advanced to the proximal end of the device and the filter is pulled proximally into it with the retained emboli capture. In this design configuration, the emboli can easily be removed for analysis afterwards.

The invention above is described as it relates to a device that can be used over a medical guidewire. The opportunity exists to configure the invention in a manner that it could in itself be used as the primary crossing device. All of the filter designs described above could be moulded onto either the over the wire or the primary crossing device as described hereunder. For a primary crossing device the filter would be bonded to a solid substrate. Some benefits would accrue in that the inner diameter onto which the filter could be wrapped down would be smaller because it would not need to move over another instrument. FIG. 18 illustrates the differences involved. The filter element 1 is mounted on the substrate shaft 33. A collapsible filter support element 50 is mounted on the substrate shaft 33 at a proximal end of the filter 1. The support element 50 has a number of foldable arms 51 which collapse against the shaft 33 for deployment and upon release extend outwardly to expand the filter 1 in the vessel.

Referring to FIGS. 20 to 22 there is shown alternative constructions of filter element comprising a compressible filter 1 shown in an expanded position with a large inlet opening 60 and smaller outlet openings 61. A collapsible wire support 62 is provided at a proximal end of the filter 1. The wire support 62 is collapsible with the filter 1 within a housing or pod for deployment and upon release expands to support the filter 1 in the vessel 4.

An alternative filter arrangement is shown in FIGS. 23 to 27. In this case, the filter comprises a Nitinol mesh which is expandable from a collapsed position shown in FIG. 23 for deployment to an expanded in use position shown in FIG. 27 to provide a filter body 65 with proximal inlet 66 and distal outlets 67.

For a primary crossing device, the distal end of the device will be flexible and atraumatic. This can be achieved by a number of means such as fabricating a spring or polymeric element to be flexible enough to deflect when it comes into contact with the walls of the vessel. The tip section would be mounted distally to the filter element. An intermediate section of the device will house the filter 1 which would be covered prior to deployment. A sheath could be fully the length of the device or attached by an actuator to a shorter sheath that covers the filter only. The proximal section of the device will provide a platform for the balloon dilatation and stent devices. The provision of a platform may be achieved as shown by removing the proximal covering to expose a wire or spring assembly. Alternatively, the whole proximal section could function as the platform. Essentially, to function as the platform for balloon catheter and stent, the devices should be sized with an outside diameter dimension that allows free movement of the catheter systems over it. Typical industry standards for coronary products permit free movement of devices over a 0.014" or 0.018" diameter while peripheral angioplasty applications use a 0.035" OD.

Referring to FIG. 28 the tubing substrates 33 onto which the filter element is bonded can move between two stoppers 63 and 64, the stoppers are mounted on the primary crossing guidewire 2. The stoppers can be manufactured from a range of metallic or polymeric components, which will permit movement of the tubing substrate 33 between them. The stoppers may also be in the form of a step in the actual medical guidewire. A large variation in distances between stoppers 63 and 64 could be made to work in this application. The stoppers are sized to prevent movement of the tubing substrate either over or under them so that they act as a stop position for the tubing substrate in both their proximal and distal locations. The stoppers can be mounted onto the primary crossing guidewire by a number of known commercial technologies; these include soldering, welding, braising, crimping and adhesive bonding. The proximal stopper will be small enough in size to fit into the internal shaft of the delivery catheter. The filter element can move axially and rotationally independently of the guidewire. This allows for good wire movement and control of filter position. The filter position will be maintained during the exchange of catheters. Any commercially known available guidewire can be adapted accordingly and used with this technique.

FIG. 29 refers to an "olive" 65; the olive component can be manufactured from a range of metallic or polymeric components such as polymeric foams, plastics, stainless steel or metal. The olive will allow a smooth transition between the guidewire 2 and the pod 3 into which the filter element is loaded and also allows for easy positioning of the filter element within the pod. The olive can be directly attached to the guidewire or it may also be attached to a tubing substrate 33. The olive can be attached to the guidewire or tubing substrate by a range of known techniques such as adhesive bonding and soldering. The olive will work as required for a range of distances distal to the filter element. A wide number of shapes and sizes could be made to work as the olive component.

Figure 30:
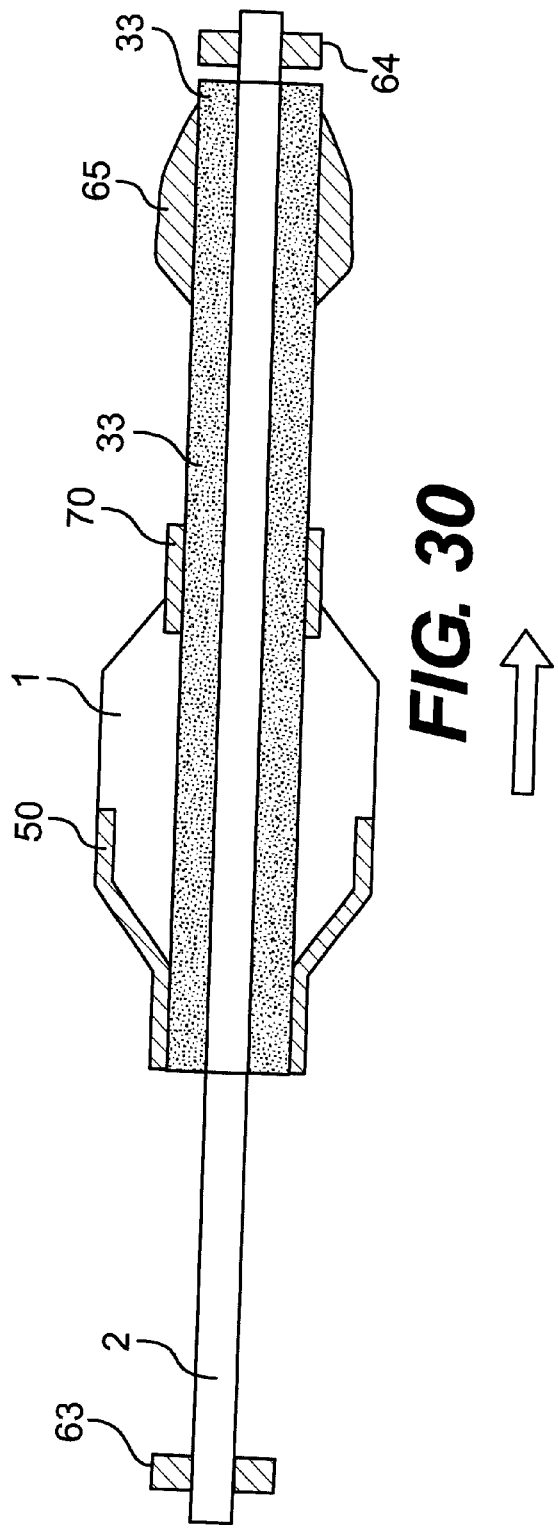
FIG. 30 is a perspective view of the filter element in its most distal position.

FIG. 30 refers to the filter element 1 when it is positioned in its most distal position. The filter element may achieve this position during loading or after deployment. The stopper element 64 prevents the filter element 1 from moving beyond it in the distal direction.

Figure 31:
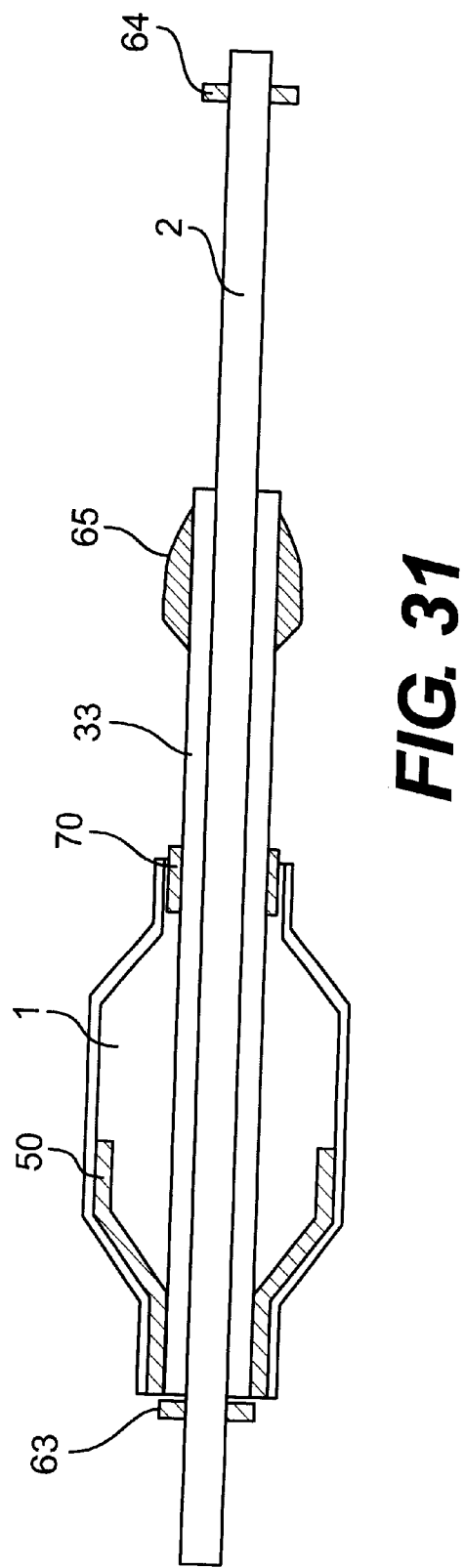
FIG. 31 is a perspective view of the filter element in its most proximal position.

FIG. 31 illustrates the filter element in its most proximal location the filter element may achieve this position when deploying the device or after deployment. The stopper element 63 prevents the filter element 1 from moving beyond it in the proximal direction.

FIG. 32 refers to a floating distal tip in this case a stopper component 66 is placed proximal to the distal end of the filter. The most distal end of the filter being fixed to a marker band 70 or other suitable substrate. The marker band 70 is not fixed to the substrate tubing 33. This allows the distal end of the filter freedom of movement in the axial direction beyond the stopper component. The stopper component can be made to work using any shape or form so as to prevent movement of the distal end of the filter in the proximal direction beyond the point of fixturing of the stopper component. The stopper component may be manufactured from metals or polymeric material, it can be joined to the tubing substrate 33 by a number of existing technologies including adhesive bonding and soldering. The stopper component 66 will work when placed in any location between 50 and 70. A floating distal tip on the filter element will facilitate the loading of the filter element into the loading pod as the filter can now extend in the axial direction and therefore be wrapped down over a greater length. This will reduce the loading force required and also reduce the profile of the loaded filter. The floating distal tip design will facilitate the loading of a large range of filter designs.

FIG. 33 refers to a concertina shaped filter with a floating distal tip. This filter geometry adds to the circumferential integrity of the filter and thus prevents the formation of creases along the length of the filter. "A" illustrates the filter as it will be when in position. "B" illustrates how the distal tip will extend in the axial direction when the filter element is loaded into a loading pod. The floating tip design can be used to accommodate the loading of many filter shape designs. For the filter design shown a longer pod is needed to accommodate the increase in axial length of the filter element when loaded.

Figure 36:
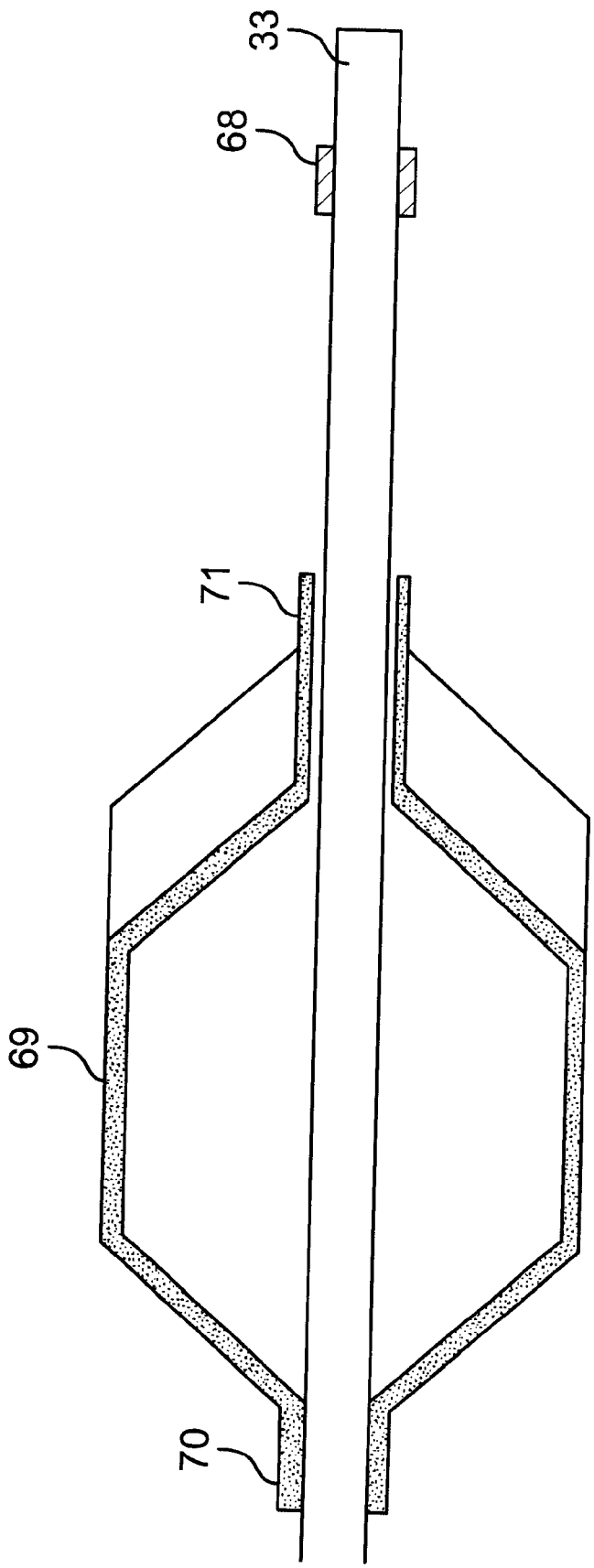
FIG. 36 is a side view of the floating distal tip design with the shape memory alloy extending from the proximal end to the distal end.

FIG. 34 relates to the floating distal tip design with a spring element 67 incorporated into the design. The spring is placed distal to the filter element. As previously illustrated in FIG. 33, the floating distal tip extends in the axial direction when loaded, the spring acts as a safety device when the filter is deployed and ensures the return of the floating distal tip to its primary location. The spring element will be soft enough to allow the distal tip to extend freely in the distal direction during loading but stiff enough to push the distal tip back to its primary location after deployment. The spring element can be manufactured from either a polymeric or metal component. The spring element can be mounted onto a substrate 33 and a stopper component used to prevent axial movement of the spring in the distal direction. Other methods of keeping the distal end of the spring element stationary could be used such as bonding, welding, crimping, soldering or crimping the distal end of the spring onto the substrate 33. This technique could also be made to work with the spring being part of the actual guidewire. There are many other configurations by which a return spring element may be incorporated into the filter as shown in FIGS. 35 and 36.

In FIG. 35 the spring element 67 is bonded to the substrate at its proximal end and the distal end of the filter element is bonded to the spring shaft. This design allows the distal end of the filter element to extend in the distal direction. The extension length could be determined by either the positioning of a stopper 68 or the stiffness of the spring. When external forces are removed from the filter the spring will return the filter to its primary location. In FIG. 36 a shape memory alloy such as nitinol is used to return the filter to its primary location. The nitinol support frame 69 is fixed to the substrate 33 at its proximal end 70 and is floating at the distal end 71. The shape memory properties of the nitinol will ensure that the filter element returns to its primary location. This design can facilitate the use of any other commercially available or known shape memory alloys. This design could also be made to work using a spring component.

Figure 37A:
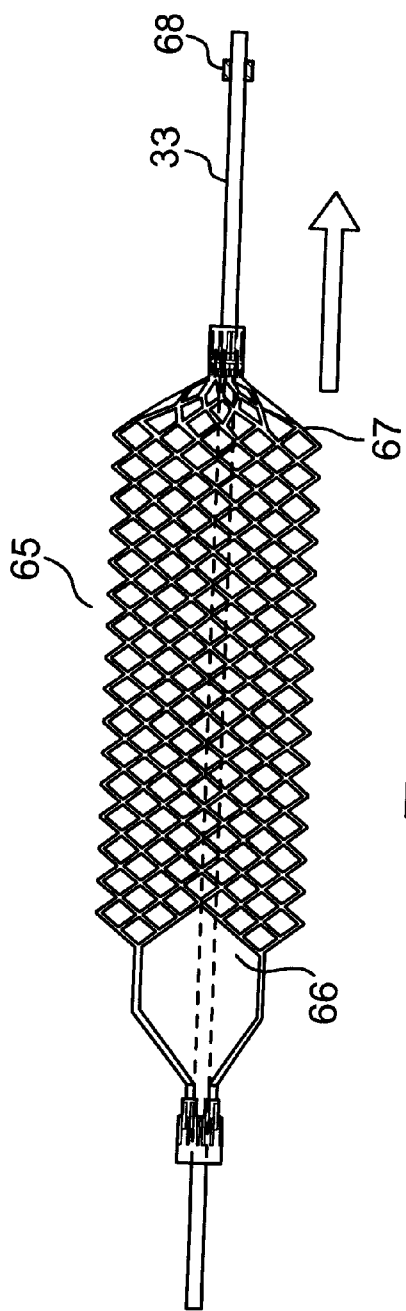
FIG. 37 is a perspective view of the mesh design incorporating a floating distal tip.
Figure 37B:
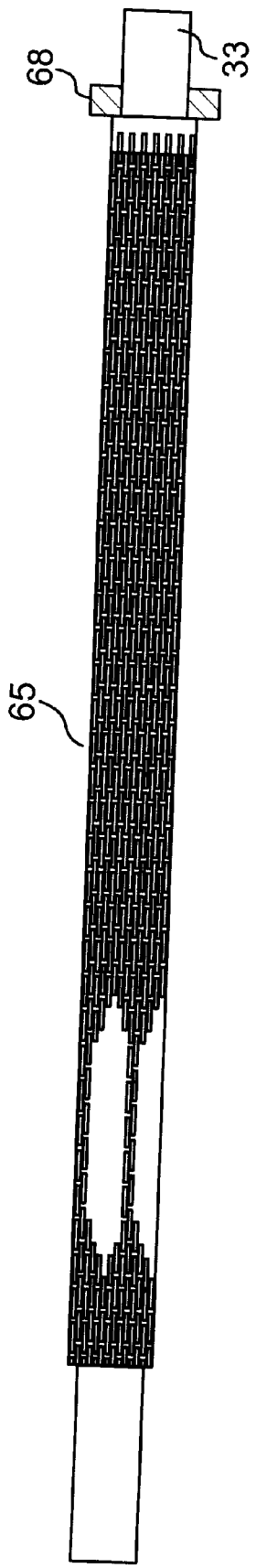
Figure 38A:
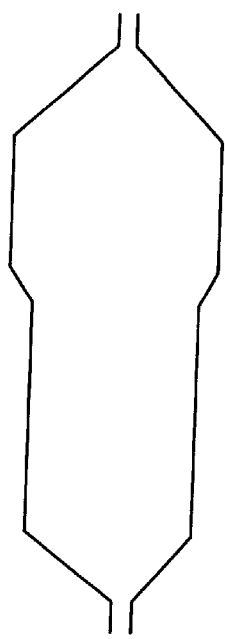
FIG. 38 illustrates perspective views of filter geometries.
Figure 38B:
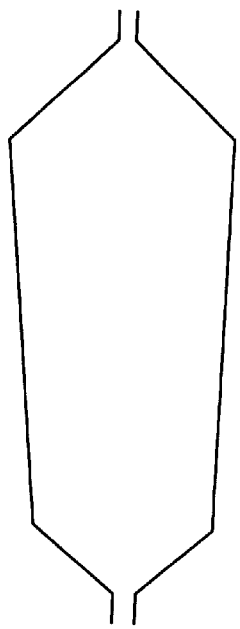
Figure 38C:
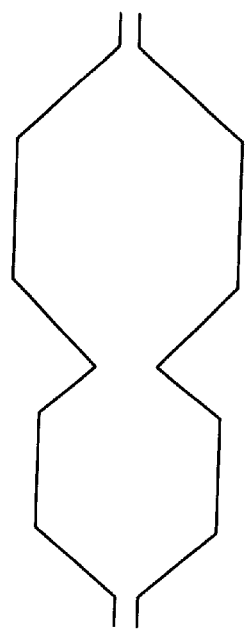
Figure 38D:
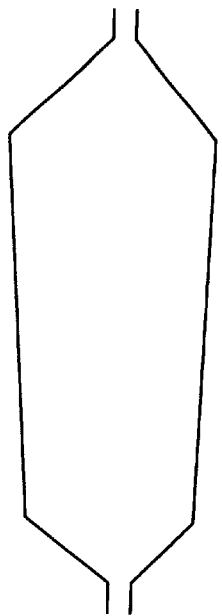
Figure 38E:
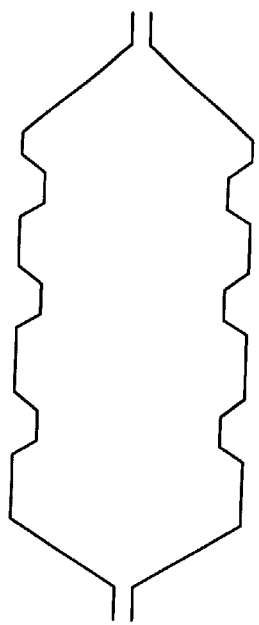
Figure 38F:
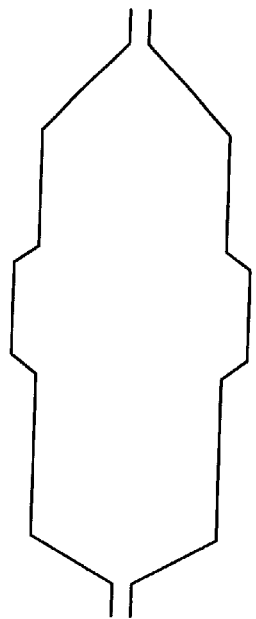
Figure 39:
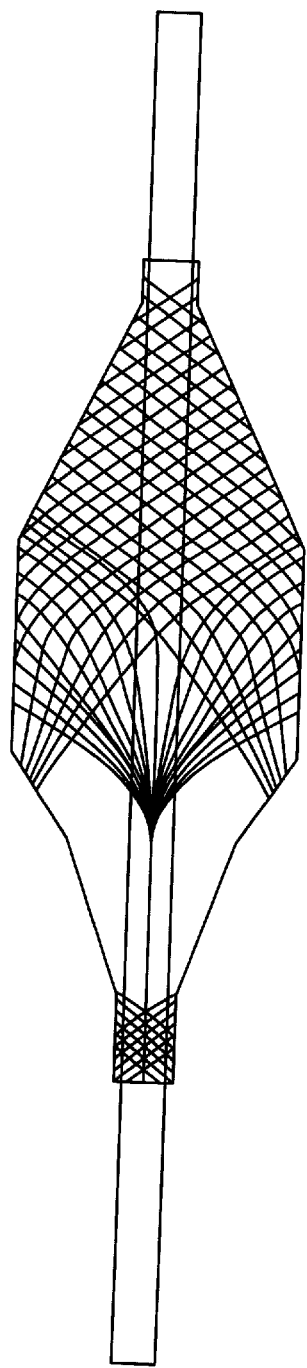
FIG. 39 shows a fibrous mesh filter design with fibres woven at the distal end and converging into a number of bundles at the proximal end.

FIG. 37 again incorporates the floating distal tip design. The filter body 65 as previously illustrated in FIG. 27 is mounted onto a substrate 33. At the proximal end the stent is fixed to the substrate. The floating distal tip design allows the filter body 65 to extend in the distal direction. As the filter body 65 extends there is a reduction in its outside diameter and an increase in its overall length. There may or may not be need for a stopper 68 as the filter body 65 will extend up to its own elastic limit which is determined by its size and geometry. The shape memory function of the filter body 65 will cause the distal tip to return to its primary location when external forces are removed from it. The proximal end of the filter body 65 may be fixed to the substrate by a number of known technologies such as bonding, soldering or crimping.

FIG. 38 illustrates a number of different filter designs which could be made to work as embolic protection devices. These filter designs all work to reduce the longitudinal length of creases which may occur should the filter be oversized, therefore acting as crease breakers. Either ends of the filters shown could act as both proximal and distal ends for the filter. The filter body may be tubular or frusto-conical.

Figure 40:
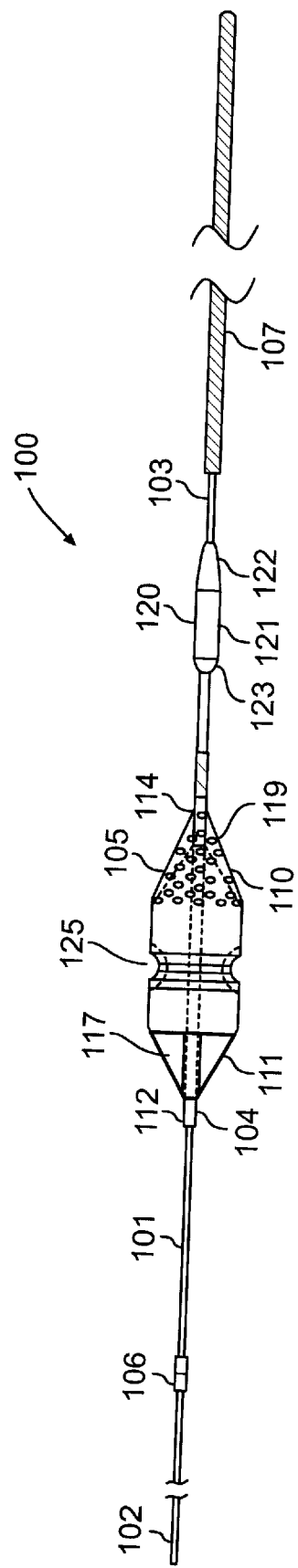
FIG. 40 is partially sectioned elevational view an embolic protection device according to the invention.

Referring to FIGS. 40 to 42 there is illustrated an embolic protection device according to the invention indicated generally by the reference number 100. The device 100 has a guidewire 101 with a proximal end 102 and a distal end 103. A tubular sleeve 104 is slidably mounted on the guidewire 101. A collapsible filter 105 is mounted on the sleeve 104, the filter 105 being movable between a collapsed stored position against the sleeve 104 and an expanded position as shown in the drawings extended outwardly of the sleeve 104 for deployment in a blood vessel.

The sleeve 104 is slidable on the guidewire 101 between a pair of spaced-apart end stops, namely an inner stop 106 and an outer stop which in this case is formed by a spring tip 107 at the distal end 103 of the guidewire 101.

The filter 105 comprises a mesh net 110 mounted over a collapsible support frame 111. The mesh net 110 is gathered into the sleeve 104 at each end, the net 110 being rigidly attached to a proximal end 112 of the sleeve 104 and the net 110 being attached to a collar 115 which is slidable along a distal end 114 of the sleeve 104. Thus the distal end of the net 110 is longitudinally slidable along the sleeve 104. The support frame 111 is also fixed at the proximal end 112 of the sleeve 104. A distal end 116 of the support frame 111 is not attached to the sleeve 104 and is thus also free to move longitudinally along the sleeve 104 to facilitate collapsing the support frame 111 against the sleeve 104. The support frame 111 is such that it is naturally expanded as shown in the drawings and can be collapsed inwardly against the sleeve 104 for loading in a catheter 118 or the like.

The filter 105 has large proximal inlet openings 117 and small distal outlet openings 119. The proximal inlet openings 117 allow blood and embolic material to enter the filter body, however, the distal outlet openings 119 allow through passage of blood but retain undesired embolic material within the filter body.

An olive guide 120 is mounted at a distal end of the sleeve 104 and has a cylindrical central portion 121 with tapered ends 122,123. The distal end 122 may be an arrowhead configuration for smooth transition between the catheter and olive surfaces. The support frame 111 is shaped to provide a circumferential groove 125 in the filter net 110. If the filter is too large for a vessel, the net may crease and this groove 125 ensures any crease does not propagate along the filter.

Enlarged openings are provided at a proximal end of the filter net 110 to allow ingress of blood and embolic material into an interior of the net 110.

In use, the filter 105 is mounted in a collapsed state within a distal end of the catheter 118 and delivered to a deployment site. When the filter is correctly positioned the catheter 118 is retracted allowing the support frame 111 to expand inflating the net 110 across the vessel in which the filter is mounted. Blood and emboli can enter the enlarged openings at a proximal end of the net 110. The blood will pass through the net wall, however, the openings or pores in the net are sized so as to retain the embolic material. After use the catheter is delivered along the guidewire 101 and slid over the filter 105 engaging the proximal inlet end 112 first to close the openings and then gradually collapsing the net against the sleeve 104 as the catheter 118 advances over the filter 105. Once the filter 105 is fully loaded in the catheter 118, it can then be withdrawn.

It will be noted that a proximal end of the filter is fixed and a distal end of the filter is longitudinally movable along the sleeve to facilitate collapsing of the filter net.

Further, the catheter engages the proximal end of the filter net first thus closing the filter net inlet and preventing escape of embolic material from the filter net as the filter net is being collapsed.

Conveniently the tip of the catheter which forms a housing or pod for reception of the filter is of an elastic material which can radially expand to accommodate the filter with the capture embolic material. By correct choice of material, the same catheter or pod can be used to deploy and retrieve the filter. For deployment, the elastic material holds the filter in a tightly collapsed position to minimise the size of the catheter tip or pod. Then, when retrieving the filter, the catheter tip or pod is sufficiently elastic to accommodate the extra bulk of the filter due to the embolic material.

Also, the filter is not fast on the guidewire and thus accidental movement of the guidewire is accommodated without unintentionally moving the filter, for example, during exchange of medical devices or when changing catheters.

It will also be noted that the filter according to the invention does not have a sharp outer edge as with many umbrella type filters. Rather, the generally tubular filter shape is more accommodating of the interior walls of blood vessels.

Conveniently also when the filter has been deployed in a blood vessel, the catheter can be removed leaving a bare guidewire proximal to the filter for use with known devices such as balloon catheter and stent devices upstream of the filter.

What is claimed is:

1. A vascular filtration device for removing embolic material in body fluid, said device comprising:

a delivery system having a longitudinal axis, distal and proximal portions, said distal portion of the delivery system being removably advanceable into the vasculature of a patient;

a collapsible filter body having a longitudinal axis, a proximity tapering proximal end and a distal end, and further having a collapsed configuration and an expanded deployed configuration, the collapsed configuration permitting delivery and withdrawal of the filter body from the vasculature of a patient;

the filter body defining an interior space when in said expanded configuration;

at least one fluid inlet on the proximal end of the filter body, the inlet being open to admit blood and embolic material into said interior space when the filter body is in the expanded configuration, and substantially closed to fluid flow when the filter body is in the collapsed configuration;

a plurality of outlet openings at the distal end of the filter body, the outlet openings being open to fluid flow from said interior space when the filter body is in the expanded configuration;

the outlet openings being sized to allow through passage of blood but retaining undesired embolic material within the filter body;

wherein the filter body is moved between the collapsed and expanded configurations through relative motion of portions of the filter delivery system with respect to the filter body;

said proximal end of the filter body being collapsible on transition to the collapsed configuration thereby firstly substantially closing said at least one fluid inlet to ensure retention of any collected embolic material in the interior space and then collapsing the remainder of the filter body; and the delivery system includes a guidewire, and the filter body is rotatable relative to the delivery system.

2. A device as claimed in claim 1, wherein said delivery system further comprises a tubular member, the filter body being moved between the collapsed and expanded configurations through relative motion of the tubular member with respect to the filter body.

3. A device as claimed in claim 1, wherein said filter body is defined by a generally elongated shape having an axial dimension greater than the transverse dimension when in an expanded configuration.

4. A device as claimed in claim 1, wherein the filter body has generally circular transverse cross sections along its longitudinal axis and an associated outer surface, and at least one of a rib and groove disposed about said associated outer surface.

5. A device as claimed in claim 1, wherein the delivery system further comprises a tubular filter retrieval device having an open distal end for reception of the filter body in the collapsed configuration, said open distal end of the filter retrieval device being engagable with the proximal end of the filter body thereby firstly substantially closing said at least one fluid inlet and being slidable relative to the filter body thereby progressively collapsing the remainder of the filter body and receiving the filter body within the retrieval device.

6. A device as claimed in claim 1, wherein said filter body is slidably disposed on the guidewire when the filter body is in said expanded deployed configuration.

7. A device as claimed in claim 6, further comprising at least one stop for limiting the range of longitudinal movement of the filter body on the guidewire.

8. A device as claimed in claim 7, wherein at least one of said at least one stop is located within the interior space when the filter body is in said expanded deployed configuration.

9. A device as claimed in claim 7, wherein the stop is mounted on the guidewire.

10. A device as claimed in claim 1, wherein the filter body is mounted on a sleeve member which is slidably disposed on said guidewire.

11. A method for the capture and removal of embolic material from a blood vessel during an interventional procedure comprising the steps of:
   preparing an embolic protection device comprising a guidewire having a proximal end and a distal end, a collapsible filter body mounted adjacent the distal end of the guidewire, the filter body having a proximally tapering proximal end and a distal end and being movable between a collapsed stored position against the guidewire and an expanded position extending laterally outwardly of the guidewire;
   sliding a catheter along the guidewire and over the filter body from a proximal inlet end of the filter to collapse and house the filter in a distal end of the catheter;
   introducing the distal end of the catheter into the vascular system of a patient;
   positioning the distal end at a desired location in the blood vessel;
   holding the guidewire and retracting the catheter to release the filter body from the catheter into the expanded position;
   filtering blood in the vessel during the interventional procedure;
   after the interventional procedure, advancing a retrieval catheter along the guidewire to engage a proximal inlet end of the filter collapsing the filter into the distal end of the cather by firstly substantially closing an inlet to the filter body to ensure retention of any collected embolic material in an interior space of the filter body and then collapsing the remainder of the filter body; and
   withdrawing the cather from the patient.

12. A device as claimed in claim 10, further including at least one stop for limiting the range of longitudinal movement of the sleeve member on the guidewire.

13. A device as claimed in claim 12, wherein said at least one stop comprises at least a first and second stop, wherein the length of the sleeve member is less than the distance between the stops.

14. A device as claimed in claim 10, wherein the sleeve member further comprises a guide olive located distal to the filter body and tapering distally and inwardly.

15. A vascular filtration device for removing embolic material in body fluid, said device comprising:
   a delivery system having a longitudinally axis, distal and proximal portions, said distal portion of the delivery system being removably advanceable into the vasculature of a patient;
   a collapsible filter body having a longitudinal axis, a proximally tapering proximal end and a distal end, and further having a collapsed configuration and an expanded deployed configuration, the collapsed configuration permitting delivery and withdrawal of the filter body from the vasculature of a patient;
   the filter body defining an interior space when in said expanded configuration;
   at least one fluid inlet on the proximal end of the filter body, the inlet being open to admit blood and embolic material into said interior space when the filter body is in the expanded configuration;
   a plurality of outlet openings at the distal end of the filter body, the outlet openings being open to fluid flow from said interior space when the filter body is in the expanded configuration;
   the outlet openings being sized to allow through passage of blood but retaining undesired embolic material within the filter body;
   wherein the filter body is moved between the collapsed and expanded configurations through relative motion of portions of the filter delivery system with respect to the filter body;
   said proximal end of the filter body being collapsible on transition to the collapsed configuration thereby firstly substantially closing said at least one fluid inlet to ensure retention of any collected embolic material in the interior space and then collapsing the remainder of the filter body; and
   the filter delivery system includes a guidewire and the filter body is detached from the delivery system so as to permit longitudinal movement of the filter body relative to the delivery system when the filter body is in the expanded deployed configuration.

16. A device as claimed in claim 15, wherein said delivery system comprises a tubular member, the filter body being moved between the collapsed and expanded configurations through relative motion of the tubular member with respect to the filter body.

17. A device as claimed in claim 15, wherein the delivery system comprises a tubular filter retrieval device having an open distal end for reception of the filter body in the collapsed configuration, said open distal end of the filter retrieval device being engageable with the proximal end of the filter body thereby firstly substantially closing said at least one fluid inlet and being slidable relative to the filter body thereby progressively collapsing the remainder of the filter body and receiving the filter body within the retrieval device.

18. A device as claimed in claim 15, wherein the detachment of the filter body from the guidewire allows for rotational movement of the filter body relative to the guidewire.

19. A device as claimed in claim 18, wherein both the proximal and distal ends of the filter body are detached from the guidewire.

20. A device as claimed in claim 18, further including at least one stop for limiting the range of longitudinal movement of the filter body on the guidewire.

21. A device as claimed in claim 20, wherein at least one of said at least one stop is located within the interior space when the filter body is in said expanded deployed configuration.

22. A device as claimed in claim 20, wherein the stop is mounted on the guidewire.

23. A device as claimed in claim 15, wherein the filter body is mounted on a sleeve member which is slidably disposed on said guidewire.

24. A device as claimed in claim 23, further including at least one stop for limiting the range of longitudinal movement of the sleeve member on the guidewire.

25. A device as claimed in claim 24, wherein said at least one stop comprises at least a first and second stop, wherein the length of the sleeve member is less than the distance between the stops.

26. A device as claimed in claim 23, wherein the sleeve member further comprises a guide olive located distal to the filter body and tapering distally and inwardly.

27. A vascular filtration device for removing embolic material in body fluid, said device comprising:

a delivery system having a longitudinal axis, distal and proximal portions, said distal portion of the delivery system being removably advanceable into the vasculature of a patient;

a collapsible filter body having a longitudinal axis, proximal and distal ends and further having a collapsed configuration and an expanded deployed configuration, the collapsed configuration permitting delivery and withdrawal of the filter body from the vasculature of a patient;

the filter body defining an interior space when in said expanded configuration;

at least one fluid inlet on the proximal end of the filter body, the inlet being open to admit blood and embolic material into said interior space when the filter body is in the expanded configuration, and substantially closed to fluid flow when the filter body is in the collapsed configuration;

a plurality of outlet openings at the distal end of the filter body, the outlet openings being open to fluid flow from said interior space when the filter body is in the expanded configuration;

the outlet openings being sized to allow through passage of blood but retaining undesired embolic material within the filter body;

wherein the filter body is moved between the collapsed and expanded configurations through relative motion of portions of the filter delivery system with respect to the filter body; and wherein the filter body has a generally circular transverse cross sections along its length forming an associated outer surface, and at least one of a protruding rib and recessed groove disposed about said associated outer surface.

28. A device as claimed in claim 27, wherein the filter body includes a said recessed groove extending 360 degrees around said associated outer surface.

29. A device as claimed in claim 27, wherein the filter body includes a said protruding rib extending 360 degrees around said associated outer surface.

30. A device as claimed in claim 27, wherein said associated outer surface forms a generally cylindrical portion between said proximal and distal end of the filter body, the cylindrical portion having a maximum axial dimension greater than a maximum transverse dimension when in the expanded configuration.

31. A device as claimed in claim 30, wherein filter body includes a tapering distal end.

32. A device as claimed in claim 27, wherein the outlet openings are generally circular.

33. A device as claimed in claim 27, wherein the filter body comprises a filter frame, the frame being movable between a collapsed position when the filter body is in a collapsed configuration and an extended outwardly projecting position in the expanded deployed configuration.

34. A device as claimed in claim 33, wherein the frame is formed of one of a shape memory and elastic memory material.

35. A device as claimed in claim 27, wherein the filter body comprises a porous barrier, the barrier forming the at least one fluid inlet and the outlet openings, the outlet openings being smaller in size than the at least one fluid inlet, and wherein the porous barrier is collapsible into a small diameter delivery catheter and is expandable upon deployment to a shape which is remembered by the porous barrier either through one of a shape memory characteristics and elastic memory characteristics.

36. A method as claimed in claim 11, wherein the filter body is slidable along the guidewire.

37. A method as claimed in claim 11, wherein the filter body is rotatable relative to the guidewire.

38. A method as claimed in claim 11, wherein the release of the filter body from the catheter allows for control of the movement of the filter body solely by movement of the guidewire.

* * * * *

UNITED STATES PATENT AND TRADEMARK OFFICE
CERTIFICATE OF CORRECTION

PATENT NO.    : 6,336,934 B1
DATED         : January 8, 2002
INVENTOR(S)   : Paul Gilson et al.

It is certified that error appears in the above-identified patent and that said Letters Patent is hereby corrected as shown below:

<u>Title page,</u>
Item [30], Foreign Application Priority Data, replace "Nov. 7, 1999" with
-- Nov. 7, 1997 --.

<u>Column 16,</u>
Line 30, replace "proximity tapering" with -- proximally tapering --;

<u>Column 17,</u>
Line 62, replace "cather" with -- catheter --;
Line 67, replace "cather" with -- catheter --; and <u>Column 18,</u>
Line 12, replace "longitudinally" with -- longitudinal --.

Signed and Sealed this

Twenty-third Day of April, 2002

Attest:

*Attesting Officer*

JAMES E. ROGAN
*Director of the United States Patent and Trademark Office*